United States Patent [19]

Guzman et al.

[11] Patent Number: 4,670,465

[45] Date of Patent: Jun. 2, 1987

[54] ARACHIDONIC ACID ANALOGS

[75] Inventors: Angel Guzman, Mexico City, Mexico; Joseph M. Muchowski, Sunnyvale, Calif.

[73] Assignee: Syntex (U.S.A.) Inc., Palo Alto, Calif.

[21] Appl. No.: 866,177

[22] Filed: May 21, 1986

[51] Int. Cl.$^4$ .................. C07C 69/92; C07C 149/40; A61K 31/19; A61K 31/235

[52] U.S. Cl. .................... 514/522; 514/544; 514/568; 558/416; 560/18; 560/64; 560/65; 560/104; 562/432; 562/473; 562/474; 562/495

[58] Field of Search ............ 562/495, 432, 473, 474; 560/18, 64, 65, 104; 558/416; 514/522, 544, 568

[56] References Cited

U.S. PATENT DOCUMENTS

| | | | |
|---|---|---|---|
| 3,705,187 | 12/1972 | Chodnekar | 562/495 |
| 3,712,913 | 1/1973 | Chodnekar | 560/18 |
| 3,829,442 | 8/1974 | Schelling | 560/64 |
| 3,832,385 | 8/1974 | Siddall | 560/18 |
| 3,833,642 | 9/1974 | Chodnekar | 560/18 |
| 4,138,579 | 2/1979 | Chodnekar | 560/64 |
| 4,482,734 | 11/1984 | Yamatsu | 562/495 |

*Primary Examiner*—Michael L. Shippen
*Attorney, Agent, or Firm*—Brian Lewis; Tom M. Moran

[57] ABSTRACT

Long chain unsaturated hydrocarbon derivatives, having from 13 to 21 carbon atoms, which are substituted at the 1-position by a phenoxy, phenylthio or a phenyl that bear a carboxylic acid group at the ortho, meta or para positions, and up to 4 carbon-carbon triple bonds, methods of preparing them, and pharmaceutical preparations containing them. These compounds are useful as lipoxygenase inhibitors, and therefore as antiinflammatory agents.

33 Claims, No Drawings

ARACHIDONIC ACID ANALOGS

BACKGROUND OF THE INVENTION

1. Field of the Invention

This invention relates to long chain unsaturated hydrocarbon derivatives, particularly those derivatives which are substituted at the 1-position by a phenoxy, phenylthio or a phenyl that bear a carboxylic acid group at the ortho, meta or para positions. This invention also relates to the use of these compounds for the treatment of diseases characterized by inflammation, to pharmaceutical compositions containing these derivatives and to processes for preparing these derivatives.

2. Related Disclosures

Arachidonic acid is a naturally occurring polyunsaturated fatty acid, also known as eicsoa-5(Z), 8(Z), 11(Z), 14(Z)-tetraenoic acid. It was first isolated from the liver and has been synthesised by several methods, see, for example, A. I. Raschlind et al, *J. Org. Chem.*, 26, 2688, (1961), and J. M. Osbond et al, *Chem. and Ind.* (London), 1959, 1288. Arachidonic acid is converted to a variety of naturally occurring compounds in the mammalian metabolism, including, for example, prostaglandins, thromboxanes, and leukotrienes. All of the major metabolic products of arachidonic acid are known to be involved in various disease states. Among the enzymes involved in this complex biochemical process, known as the "arachiodonic acid cascade", are fatty acid cyclooxygenase and lipoxygenase. A more complete discussion of the arachidonic acid cascade can be found at *Chem. and Eng. News*, Aug. 16, 1982, 30–44. Certain arachidonic acid derivatives have been prepared. These include eicosa-5,8,11,14-tetraynoic acid, disclosed by J. M. Osbond et al, *J. Chem. Soc.*, 2779 (1961); eicosa-8(Z),11(Z),14(Z)-trien-5-ynoic acid, described by H. Heslinger et al. in *Recueil*, 94, 262 (1975); nonadeca-5(Z),8(Z),11(Z),14(Z)-trien-5-ynoic acid described by R. K. Beerthuis et al. in *Recueil*, 87, 461 (1968); and octadeca-5,8,11,14-tetraynoic acid described by R. K. Beerthuis et al. in *Recueil*, 90, 943 (1971).

A new family of unsaturated carboxylic acid derivatives related to arachidonic acid have now been discovered. These compounds inhibit lipoxygenase and are useful for treating disease states characterized by inflammation.

SUMMARY OF THE INVENTION

One aspect of this invention is a compound represented by the formula:

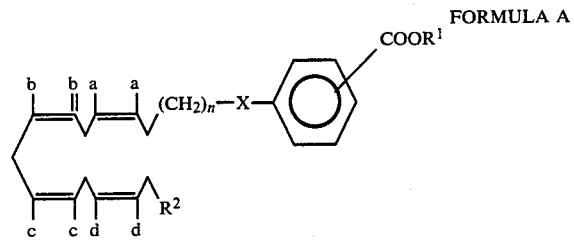

FORMULA A wherein:
n is an integer equal to zero, 1, 2 or 3;
X is S, O, or $CH_2$;
$R^1$ is hydrogen, lower alkyl or a pharmaceutically acceptable cation;
$R^2$ is lower alkyl or

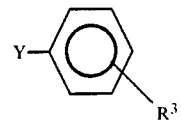

wherein Y is —O— or —S—; and $R^3$ is hydrogen, lower alkyl, lower alkoxy, lower alkylthio, halo, cyano or trifluoromethyl and each of the pairs of a—a, b—b, c—c, and d—d is independently hydrogens or a covalent bond.

Another aspect of this invention is a pharmaceutical composition that comprises a compound of formula (A) in combination with a pharmaceutically acceptable excipient.

Still another aspect of this invention is the treatment of a mammal having a disease state characterized by inflammation which method comprises administering a therapeutically effective amount of a compound of formula (A) to the mammal.

Still another aspect of this invention is the preparation of a compound of formula (A).

DESCRIPTION OF PRESENTLY PREFERRED EMBODIMENTS

Definitions

As used herein the term "alkyl" means a branched or unbranched saturated hydrocarbon chain. Examples include methyl, ethyl, propyl, tert-butyl, neo-pentyl, n-hexyl, and the like.

As used herein the term "alkoxy" means the group —OR wherein R is alkyl as defined above. Examples include methoxy, ethoxy, propoxy, tert-butoxy, neo-pentyloxy, n-hexyloxy, and the like.

As used herein the term "alkylthio" refers to the group —SR in which R is alkyl as defined above.

As used herein the term "halo" refers to chloro, bromo, or iodo.

As used herein the term "lower" modifies alkyl and alkoxy, and refers to those radicals having six carbon atoms or less.

As used herein the term "optional" or "optionally" means that the subsequently described event or circumstance may or may not occur, and that the description includes instances where said event or circumstance occurs and instances in which it does not.

As used herein the term "optionally followed by converting the acid to the salt" means that said conversion may or may not be carried out in order for the process described to fall within the invention, and the invention includes those processes wherein the acid is converted to the salt and those processes in which it is not.

As used herein the term "pharmaceutically acceptable cation" refers to a cation derived from pharmaceutically acceptable non-toxic bases, including inorganic and organic bases.

Cations derived from inorganic bases include sodium, potassium, lithium, ammonium, calcium, magnesium, ferrous, zinc, copper, manganous, aluminum, ferric, and manganic cations, and the like. Particularly preferred are the ammonium, potassium, sodium, calcium, and magnesium cations.

Cations derived from pharmaceutically acceptable organic non-toxic bases include cations of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, N-methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

Compounds of formula (A) where $R^1$ is a pharmaceutically acceptable cation are prepared by conventional procedures, e.g. by reacting an organic solution of the compound with a solution of a suitable base to obtain a base addition salt either by precipitation, or by evaporation of the solution.

When optical isomers are possible, for example with asymmetric branched alkyl groups, each isomer, the racemic mixture and mixtures that are not racemic fall within the scope of the claims.

The term "treatment" as used herein covers any treatment of a disease in a mammal, and includes:

(i) preventing the disease, that is, causing the clinical symptoms of the disease not to develop;

(ii) inhibiting the disease, that is, arresting the development of clinical symptoms; or (iii) relieving the disease, that is, causing regression of clinical symptoms.

Presently Preferred Embodiments

The preferred compounds object of the present invention are represented by the formulas:

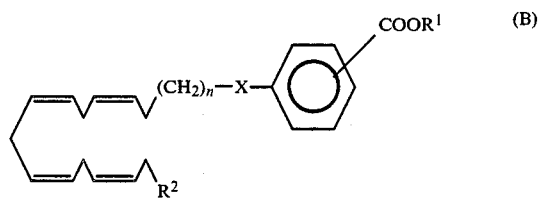
(B)

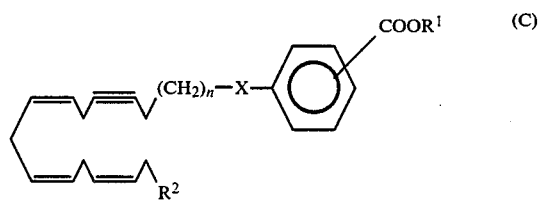
(C)

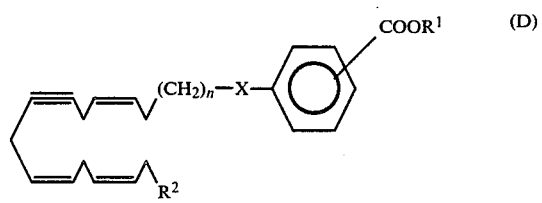
(D)

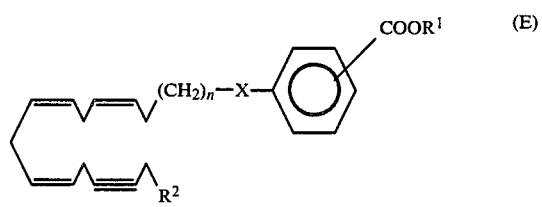
(E)

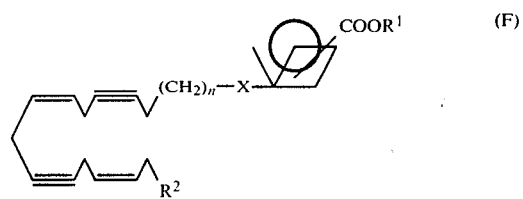
(F)

wherein n, X, $R^1$ and $R^2$ are as defined in the Summary of the Invention above.

Representative compounds of formula (A) are:

| n | X | position of $R^1$ as the acid | $R^2$ | a-a | b-b | c-c | d-d |
|---|---|---|---|---|---|---|---|
| 1 | zero | S | 2-carboxy | $C_5H_{11}$ | H | H | H | H |
| 2 | zero | S | 3-carboxy | $C_5H_{11}$ | H | H | H | H |
| 3 | zero | S | 4-carboxy | $C_5H_{11}$ | H | H | H | H |
| 4 | zero | S | 2-carboxy | $C_5H_{11}$ | cb | H | H | H |
| 5 | zero | S | 3-carboxy | $C_5H_{11}$ | cb | H | H | H |
| 6 | zero | S | 3-carboxy | $C_5H_{11}$ | H | cb | H | H |
| 7 | zero | S | 4-carboxy | $C_5H_{11}$ | H | cb | H | H |
| 8 | zero | S | 2-carboxy | $C_5H_{11}$ | cb | H | cb | H |
| 9 | zero | S | 4-carboxy | $C_5H_{11}$ | cb | H | cb | H |
| 10 | 3 | S | 2-carboxy | $C_5H_{11}$ | H | H | H | H |
| 11 | zero | S | 2-carboxy | —O—Ph | H | H | H | H |
| 12 | zero | S | 3-carboxy | —O—Ph | H | H | H | H |
| 13 | zero | S | 2-carboxy | —O—Ph | cb | H | H | H |
| 14 | zero | S | 3-carboxy | —O—Ph | H | H | H | cb |
| 15 | zero | S | 4-carboxy | —O—Ph | H | H | H | cb |
| 16 | zero | O | 2-carboxy | —O—Ph | H | H | H | H |
| 17 | zero | O | 3-carboxy | —O—Ph | H | H | H | H |
| 18 | zero | O | 2-carboxy | $C_5H_{11}$ | H | H | cb | H |
| 19 | zero | O | 2-carboxy | $C_5H_{11}$ | H | H | H | H |
| 20 | zero | O | 4-carboxy | $C_5H_{11}$ | H | cb | H | H |
| 21 | zero | $CH_2$ | 2-carboxy | $C_5H_{11}$ | H | H | H | H |
| 22 | zero | $CH_2$ | 2-carboxy | $C_5H_{11}$ | cb | H | H | H |

Where O indicates an oxygen atom, S indicates a sulfur atom, H indicates two hydrogen atoms, Ph indicates an optionally phenyl group, and cb indicates a covalent bond.

Utility and Administration

The compounds of this invention are useful for treating mammals having a variety of disease states characterized by overproduction of the products of the lipoxygenase metabolism of arachidonic acid. Disease states that may be treated include inflammatory diseases including rheumatoid arthritis, inflammatory bubble disease; psoriasis; various cardiovascular syndromes, particularly those characterized by inappropriate clotting of the blood, such as thrombosis, and the like; and hypersensitivity diseases, such as asthma.

Generally, the diseases characterized by overproduction of the products of the lipoxygenase pathway of arachidonic acid metabolism of are found in mammals including domestic commercial animals such as horses, cattle, sheep and pigs; dosmetic house animals such as dogs, cats and the like; and particularly humans.

In vitro lipoxygenase inhibiting activity of the compounds of this invention are determined by the standard Human Polymorphonuclear Leukocytes assay. This assay is a modification of that described by O. Radmark, C. Malmasten, and B. Samuelsson in *Febs Letter*, 110, 213–215. In vivo lipoxygenase inhibiting activity of the compounds of this invention are determined by the croton oil rat ear inflammation assay as described by G.

Tonelli, L. Thidould, and I. Ringler in *Endocrinology*, 77, 625–634 (1965).

The compounds of this invention are administered at a therapeutically effective dosage, i.e. a dosage sufficient to inhibit the activity of lipoxygenase. Administration of the active compounds and salts described herein can be via any of the accepted modes of administration for agents that are antiinflammatory agents. Depending on the specific disease state, administration can be systemic, via parenteral, oral, intravenous, or nasal routes; or topical.

The compounds of this invention are generally administered as a pharmaceutical composition which comprises a pharmaceutical excipient in combination with a compound of formula (A). Depending on the type of composition, the compound of formula (A) is present in an amount ranging from about 0.5 wt% to 95.0 wt% with an excipient in the range of about 99.5 wt% to 5.0 wt%.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. Liquid pharmaceutically administerable compositions can, for example, be prepared by dissolving, dispersing, etc. an active compound as defined above and optional pharmaceutical adjuvants in a carrier, such as, for example, water, silane, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 18th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

For systemic administration via suppository, traditional binders and carriers include, e.g. polyalkalene glycols or triglycerides. Such suppositories may be formed from mixtures containing active ingredient in the range of 0.5%–10%; preferably 1–2%.

Methods of Preparation

The novel compounds of formula (A) in which a—a, b—b, c—c and d—d are double bonds, that is, the compounds of formula (B), and those in which a—a is a triple bond and b—b, c—c and d—d are double bonds, that is, the compounds of formula (C) can be prepared by a method illustrated by REACTION SCHEME I:

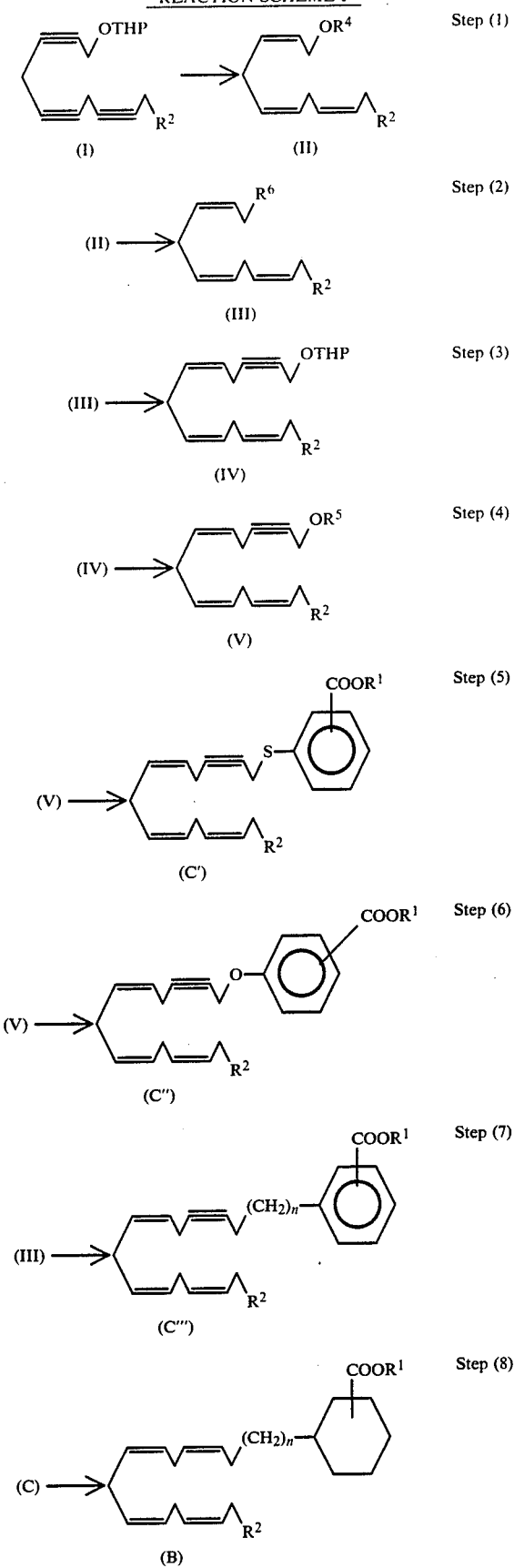

-continued
REACTION SCHEME I

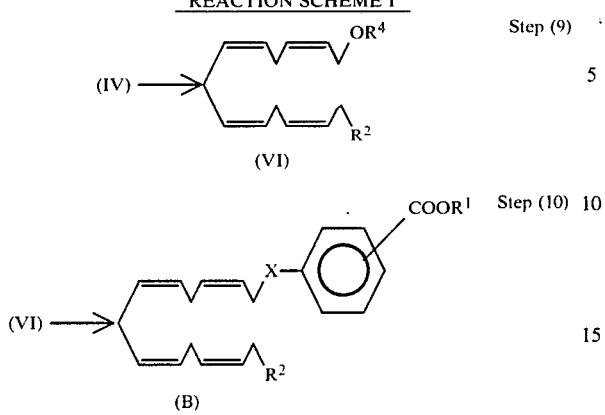

Step (9)

Step (10)

wherein:

X is O, S, or $CH_2$;
$R^1$ is hydrogen or lower alkyl;
$R^2$ is straight chain lower alkyl or optionally substituted phenyl ether or phenyl thio ether;
$R^4$ is tetrahydropyranyl, hydrogen or $SO_2CH_3$;
$R^5$ is hydrogen or $SO_2CH_3$;
$R^6$ is bromo or iodo; and
$R^7$ is lower alkyl.

The starting compounds (I) are known, or can be prepared by known methods. Thus, the tetrahydropyranyl ethers of undeca-2,5,8-triyn-1-ol and tetradeca-2,5,8-triyn-1-ol have been disclosed by D. Van der Steen et al in *Recueil*, 82, 1015 (1963), and the preparation of trideca-2,5,8-triyn-1-ol tetrahydropyranyl ether has been described by R. K. Beerthuis et al in *Recueil*, 87, 461 (1968).

Pentadeca-2,5,8-triyn-1-ol tetrahydropyranyl ether can be prepared by coupling propargyl alcohol tetrahydropyranyl ether with n-hexyl bromide in the presence of lithium amide, to produce 2-nonyn-1-ol tetrahydropyranyl ether, then hydrolysing of the tetrahydropyranyloxy function with Pyr/PTS in ethanol solution followed by esterification of the hydroxy compound with methanesulfonyl chloride in the presence of triethylamine. The mesylate is then reacted with lithium bromide in acetone solution to produce 1-bromo-2-nonyne. Finally the latter compound is coupled with hexa-2,5-diyn-1-ol-tetrahydropyranyl ether in the presence of ethylmagnesium bromide and cuprous chloride. The sequence of reaction conditions are essentially the same as those described hereinafter in detail.

Compound (I) where $R^2$ is optionally substituted phenoxy or optionally substituted phenylthio can be prepared by monoetherification of 2-butyne-1,4-diol with dihydropyran in the presence of an acid catalyst such as p-toluenesulfonic acid, esterification of the free hydroxyl group with methanesulfonyl chloride, reaction of the mesylate with lithium bromide in acetone solution, to produce 1-bromo-but-2-yn-4-ol tetrahydropyranyl ether. Condensation of the latter compound with phenol, thiophenol or an optionally substituted derivative thereof produces the corresponding 1-iodo-4-substituted-but-2-yne. This condensation is effected via the formation of the sodium phenolate or thiophenolate. The tetrahydropyranyloxy moiety of the 1-bromo-but-2-yn-4-ol tetrahydropyranyl ether is hydrolysed, the hydroxyl group esterified with methanesulfonyl chloride, followed by treatment of the mesylate with sodium iodide in the presence of sodium bicarbonate, which is coupled with hexa-2,5-diyn-1-ol tetrahydropyranyl ether in the presence of ethylmagnesium bromide.

STEP (1) of the above-depicted process involves catalytic partial hydrogenation of a 1-tetrahydropyranyloxy-triyne compound of formula (I) to the corresponding all cis triene, (II) where $R^4$ is tetrahydropyranyl. This stereospecific reduction is preferably conducted in the presence of Lindlar's catalyst partially deactivated by quinoline, in a suitable solvent or mixture of solvents, at room temperature and atmospheric pressure, until 3-molar equivalents of hydrogen are consumed. Suitable solvents for this reduction are polar solvents such as lower aliphatic alcohols, for example, methanol, ethanol, isopropanol and the like, ethyl acetate, or mixtures of alcohols and ethyl acetate.

In the preferred embodiments, this hydrogenation is conducted using from 5 to 15% by weight of catalyst and from 2 to 15% by volume of quinoline, in anhydrous methanol.

Alternatively, Lindlar's catalyst doped with a salt such as $MnCl_2$, $CdCl_2$, $SnCl_2$ or nickel-boride catalyst modified with a small amount of copper, or 10% palladium on barium sulfate catalysts can also be used.

Then the tetrahydropyranyloxy function is hydrolyzed by treatment with about 0.1 to 0.5 molar equivalents of pyridinium-p-toluenesulfonate (Pyr/PTS) in ethanol solution, at a temperature comprised between 40° C. to 60° C., preferably at about 55° C. for about 1 to 4 hours, preferably for about 2 hours, to produce the corresponding hydroxy triene (II), where $R^4$ is H. This hydrolysis can also be effected with p-toluenesulfonic acid, at room temperature for about 2 hours.

Then the hydroxyl group is esterified with methanesulfonyl chloride in the presence of a tertiary amine base such as triethylamine, pyridine and the like, preferably triethylamine, in an anhydrous inert aprotic solvent, using preferably methylene chloride, to produce the corresponding mesylate (II) where $R^4$ is $SO_2CH_3$. The reaction is carried out at $-10°$ C. to 10° C., preferably at 0° C., for about 20 minutes to 1 hour, using from 1.1 to 2 molar equivalents of methanesulfonyl chloride and triethylamine, preferably about 1.3 molar equivalents of each reagent per mole of hydroxy compound.

In STEP (2), compound (II), where $R^4$ is $SO_2CH_3$, is reacted with an excess of an alkali metal halide, such as lithium bromide or sodium iodide, to produce the corresponding 1-halo derivative, compound (III). In the case of the bromo compounds from 5 to 10 molar equivalents of lithium bromide are used, preferably about 7 molar equivalents. The reaction is conducted in, for example, acetone solution, at room temperature or under slight heating, for a period of time of about 20 minutes to about 2 hours, preferably at room temperature for about 45 minutes. When sodium iodide is employed, from 2 to 6 molar equivalents of reagent are used per mole of mesylate, preferably about 3 molar equivalents. The reaction is conducted in the presence of a stoichiometric amount of an alkali metal bicarbonate such as sodium bicarbonate, in acetone solution, under essentially the same reaction conditions as those previously described for obtaining the bromo compound.

In conducting STEP (3), compound (III) is coupled with the tetrahydropyranyl ether of propargyl alcohol, via formation of the Grignard reagent, in the presence of cuprous ion, to produce the corresponding 1-tetrahydropyranyloxy-5,8,11-trien-2-yne compound (IV). The reaction is conducted under anhydrous conditions in an ether solvent, for example, tetrahydrofuran, diethyl ether, 1,2-dimethoxyethane and the like, or mixtures thereof, under an inert atmosphere, at a temperature between $-20°$ C. to the reflux temperature of the solvent for an overall period of between 4 to 8 hours. Initially, a solution of the tetrahydropyranyl ether of propargyl alcohol in an anhydrous ethereal solvent, using preferably tetrahydrofuran as solvent, is treated with 1-1.1 molar equivalents of a Grignard reagent such as a 3-4N ethereal solution of ethylmagnesium bromide, at a temperature of about $-10°$ C. to 10° C., preferably at about 0° C., under an argon or nitrogen atmosphere. The mixture is refluxed for a short period of time, of the order of 30 minutes to 2 hours, preferably for about 1 hour, to form the Grignard reagent, which is immediately coupled with compound (III) in the same reaction medium, in the presence of catalytic amounts of a cuprous salt such as cuprous chloride, cuprous bromide, cuprous iodide or cuprous cyanide. The preferred source of cuprous ion for this reaction is cuprous chloride.

This coupling is preferably conducted at reflux temperature for a period of time sufficient to complete the reaction, of the order of 2 to 5 hours, preferably for about 3 hours. Although varying proportions of reactants may be employed, it is preferred to use a 2:1 molar ratio of propargyl alcohol tetrahydropyranyl ether: compound (III).

In STEP (4) the tetrahydropyranyloxy function in compound (IV) is hydrolyzed with Pyr/PTS in ethanol solution, essentially under the same reaction conditions described hereinabove in STEP (1), and the hydroxy compound thus obtained, compound (V) where $R^5$ is H is then esterified with methanesulfonyl chloride in methylene chloride solution, in the presence of triethylamine, by using the reaction conditions described in STEP (3), to produce the corresponding mesylate (V) where $R^5$ is $SO_2CH_3$.

Finally, in the condensation of STEPS (5) and (6) the type of reagent and reaction conditions will determine the product obtained. Thus, when the crude mesylate is reacted in STEP (5) with a lower alkyl ester, preferably, the methyl ester of a mercaptobenzoic acid (ortho, meta or para isomer) in the presence of an alkali metal alkoxide, preferably sodium methoxide in methanol solution, there are readily obtained the compounds of formula C', the alkyl esters of o-, m- or p-thiosubstituted benzoic acids where $R^1$ is alkyl.

This reaction is conducted under anhydrous conditions, at a temperature between 0° C. and 40° C., preferably at room temperature, for a short period of time, of the order of 10 minutes to 1 hour, preferably for about 30 minutes. There are used about 2.5 to 3 molar equivalents of sodium alkoxide as condensing agent, and from 1.1 to 2 molar equivalents, preferably about 1.3 molar equivalent, of the mercaptobenzoic acid ester.

In STEP (6), the compounds of formula C", in which X is O and $R^1$ is alkyl are obtained by condensing a mesylate of formula (V) when $R^5$ is $SO_2CH_3$ with an alkyl ester, preferably the methyl ester of a salicylic acid (o-, m- or p-isomer) in the presence of sodium hydride. The reaction is also conducted under anhydrous conditions, in an aprotic solvent such as dimethylformamide, preferably at room temperature, for a period of time of the order of 1 to 10 hours, preferably for about 2 to 6 hours. About 1 to about 3 molar equivalents of both sodium hydride and alkyl salicylate are used, preferably about 2 molar equivalents per mole of starting methanesulfonate.

In STEPS (5) and (6), the alkyl ester compounds are hydrolyzed to the corresponding free acids by alkaline treatment, that is, by treatment with an excess of an alkali metal hydroxide or an alkali metal carbonate, such as sodium hydroxide, potassium hydroxide, lithium hydroxide, sodium carbonate, potassium carbonate and the like, in a lower aqueous aliphatic alcohol, optionally in admixture with a small amount of tetrahydrofuran, using particularly 0.5N sodium hydroxide in 90% methanol. The reaction is preferably conducted at room temperature, for a period of time between about 15 to 72 hours, depending upon the starting compound.

When lithium hydroxide is employed, the preferred solvent is aqueous dimethoxyethane. About 4 to 10 molar equivalents of the reagent are used, preferably about 6 molar equivalents. When necessary, the reaction can be taken to completion under a slight heating, that is, at about 40° C.

The 1-sulfonyloxy-tetraenyl compounds of formula (VI), when $R^4$ is $SO_2CH_3$ are prepared from the 1-tetrahydropyranyloxy-5(Z),8(Z),11(Z)-trien-2-yne compounds of formula (IV). These compounds are selectively and partially hydrogenated in the presence of Lindlar's catalyst until the absorption of 1 molar equivalent of hydrogen is complete, thereby hydrogenating the acetylenic linkage to a cis olefin The tetrahydropyranyloxy function is then hydrolysed with Pyr/PTS in ethanol solution and esterification of the hydroxyl group with methanesulfonyl chloride is carried out STEP (9) under essentially the same reaction conditions described hereinabove in detail for STEP (1).

Upon condensation of the mesylates thus obtained (compound (VI) when $R^4$ is $SO_2CH_3$) with a lower alkyl ester of an o-, m- or p-mercaptobenzoic acid, an alkyl ester of an o-, m- or p-salicylic acid, phenol or thiophenol, as previously described in STEP (5) the corresponding all cis tetraenyl compounds (B) are obtained. When applicable, in STEP (10) the alkyl ester group is hydrolyzed with a base, essentially as described in STEP (5) above.

The compounds of formulas (B) and (C) in which X is $(CH_2)_n$ and n is 1, 2 or 3 are obtained as follows:

In STEP (7), a 1-halo triene (III), preferably the iodo compound, is coupled with a benzoic acid ester derivative substituted at the ortho, meta or para position by an ω-alkynylalkyl radical of 4 to 7 carbon atoms in a suitable inert organic solvent and in the presence of a source of cuprous ions, to produce the corresponding trien-ynyl substituted benzoic acid ester compound (C''') where $R^1$ is alkyl. The reaction is conducted under anhydrous conditions and under argon or nitrogen atmosphere. Initially, a solution of an ω-alkynylalkyl radical substituted benzoic acid ester, such as 2-(3-butyn-1-yl)benzoic acid methyl ester in an ethereal solvent, preferably tetrahydrofuran, is reacted with an equimolecular amount of n-butyl lithium in hexane solution, at a temperature of about $-70°$ C., for a period of time of about 30 minutes to 2 hours, preferably for about 45 minutes, followed by the addition of catalytic amounts of a cuprous salt, preferably cuprous iodide. After a few minutes, a solution of the iodo compound of formula (III) in tetrahydrofuran is added. The mixture is stirred at $-70°$ C. to 0° C., preferably, at $-20°$ C. for about 1 to 5 hours, preferably for about 2 hours. Preferably a 2:1:1 molar ratio of the ω-alkynylalkyl radical substituted benzoic acid ester:iodo compound (III):and cuprous iodide is used.

The o-, m- or p-ω-alkynylalkyl substituted benzoic acid ester reagents for example, 2-(3-butyn-1-yl)-benzoic acid methyl ester can be prepared by reacting o-methylbenzoic acid (o-toluic acid) with 2 molar equivalents of allyl bromide in the presence of n-butyl lithium and diisopropylamine, in accordance with the method of P. L. Creger et al, *J. Am. Chem. Soc.*, 92, 1396 (1970) followed by esterification of the carboxylic acid group with diazomethane, to produce 2-(3-buten-1-yl)-benzoic acid methyl ester, which is converted into the alkynyl compound via bromination of the double bond followed by strong alkaline treatment, acidification, extraction and reesterification with diazomethane. The alkyl ester moiety is hydrolyzed with base, using preferably lithium hydroxide as described in STEP (5), to produce the free acids, $R^1$ being H.

In STEP (8), the acetylenic linkage in compounds of formula (C) where $R^1$ is alkyl is hydrogenated in the presence of Lindlar's catalyst and quinoline until the absorption of 1 molar equivalent of hydrogen. The alkyl ester group is in turn hydrolyzed by alkaline treatment, as described hereinbefore for STEP (5).

The compounds of formula (F) can be prepared by the method of REACTION SCHEME I, STEPS 1 through 7 starting, for example, from the compound tetradeca-2(Z),8(Z)-di-en-5-yn-1-ol, described in U.S. Pat. No. 4,497,827, is treated with about 1.5 molar equivalents of methanesulfonyl chloride and triethylamine, as described in detail in STEP (1), to produce the mesylate. The latter compound is converted into a 1-halo compound, preferably the iodo compound, by reaction with at least a stoichiometric amount of sodium iodide in the presence of sodium bicarbonate, in acetone solution (STEP (2)). The 1-iodotetradeca-2(Z),8(Z)-dien-5-yne thus obtained is coupled with the Grignard reagent of propargyl alcohol tetrahydropyranyl ether (STEP (3)), yielding heptadeca-5(Z),11(Z)-diene-2,8-diyn-1-ol tetrahydropyranyl ether (Compound VII where $R^2$ is n-butyl and $R^8$ is tetrahydropyranyl).

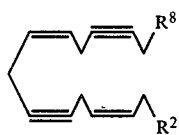

(VII)

wherein $R^2$ has the meaning indicated in the summary of the invention above, and $R^8$ is halo, tetrahydropyranyl, or methanesulfonyl.

The tetrahydropyranyloxy function is hydrolyzed, preferably with from 0.1 to 0.5 molar equivalents of Pyr/PTS in ethanol solution, and the hydroxyl group esterified with methanesulfonyl chloride (STEP (4)) to yield heptadeca-5(Z),11(Z)-diene-2,8-diyn-1-ol methanesulfonate (Compound VII where $R^2$ is n-butyl and $R^8$ is methanesulfonate).

Upon condensation of the latter mesylate with an ester of an o-, m- or p-mercaptobenzoic acid or an o-, m- or p-salicylic acid, preferably the methyl esters in the presence of sodium methoxide there are obtained the corresponding alkyl esters of 2-, 3- or 4-(heptadeca-5'(Z),11'(Z)-diene-2',8'-diynylthio)benzoic acid or 2-, 3- or 4-(heptadeca-5'(Z),11'(Z)-diene-2',8'-diynyloxy)benzoic acid, both compounds which are represented by formula F, respectively.

The esterified products are converted into the free acids by alkaline treatment followed by acidification (STEP (5)).

By coupling of for example 1-iodotetradeca-2(Z),8(Z)-diene-5-yne (STEP (2)) with an ω-alkynylalkyl substituted benzoic acid ester in the presence of n-butyl lithium and cuprous iodide (STEP (7)) there are obtained the corresponding diene- diyne-benzoic acid esters in which n is 1, 2 or 3, depending upon the reagent used. Thus for example, when the reagent is 2-(3-butyn-1-yl)benzoic acid methyl ester there is obtained 2-(octadeca-6'(Z),12'(Z)-diene-3',9'-diynyl)benzoic acid methyl ester. The free acids are obtained by alkaline treatment of the esters followed by acidification (STEP (5)).

The reaction conditions used, that is, proportion of reagents, temperature and reaction time are within the ranges set forth in REACTION SCHEME I.

The compounds of formula (D) in which a—a, c—c and d—d are double bonds and b—b is a triple bond, X is S or O and n is zero can be prepared by a process illustrated by Reaction Scheme II.

REACTION SCHEME II

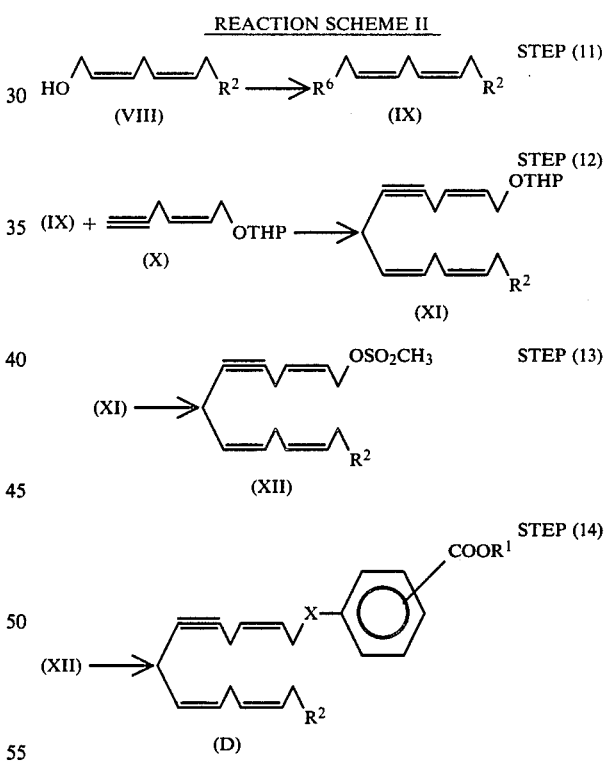

wherein $R^1$, $R^2$, $R^6$ and X are as defined in REACTION SCHEME I above.

The starting materials for STEP (11) are the 1-hydroxyalka-2(Z),5(Z)-dienes or 1-hydroxyhepta-2(Z),5(Z)-dienyl phenyl ethers or thioethers, (VIII). Thus for example, undeca-2(Z),5(Z)-dien-1-ol [J. A. Gleason et al, *Tetrahedron Letters*, 21, 1129 (1980)] is converted into a 1-halo derivative (IX) via esterification of the hydroxyl group with methanesulfonyl chloride followed by treatment of the crude mesylate with an alkali metal halide, preferably sodium iodide. These reactions are carried out employing the same proportion of reagents, reaction conditions and techniques described in REACTION SCHEME I, STEPS 1 and 2.

In STEP (12), the halo compounds (IX) are coupled with hex-2(Z)-en-5-yn-1-ol tetrahydropyranyl ether (X), disclosed in U.S. Pat. No. 4,497,827, via formation of its Grignard reagent, to produce the corresponding 1-tetrahydropyranyloxy-2(Z),8(Z),11(Z)-trien-5-yne compound of formula (XI), for example, heptadeca-2(Z),8(Z),11(Z)-trien-5-yn-1-ol tetrahydropyranyl ether. In general, the reaction conditions are those described herein before in STEP (3), however, in the preferred embodiments, about 1.1 to 2 molar equivalents of the halo compound (IX) are used per mole of hex-2(Z)-en-5-yn-1-ol tetrahydropyranyl ether. The bromomagnesium salt of the latter is preferably formed at room temperature.

In STEP (13) the tetrahydropyranyloxy function is then hydrolyzed with Pyr/PTS in ethanol solution, and the hydroxy compound esterified with methanesulfonyl chloride in the presence of triethylamine, by using essentially the reaction conditions of STEP (1) above, to produce the mesylate (XII), for example, heptadeca-2(Z),8(Z),11'(Z)-trien-5-yn-1-ol methanesulfonate.

In STEP (14), conversion of the latter mesylates into the corresponding o-, m- or p-substituted benzoic acid ester derivatives of compound D where $R^1$ is alkyl and thence to the free acids, where $R^1$ is H, for example, 4-(heptadeca-2'(Z),8'(Z),11'(Z)-trien-5'-ynylthio)benzoic acid is achieved using the same reagents and reaction conditions described in detail in STEPS (6) and (7) of REACTION SCHEME I.

The compounds of formula (E), where X is S or O, n is zero and $R^2$ is n-butyl can be prepared in accordance with REACTION SCHEME III.

REACTION SCHEME III

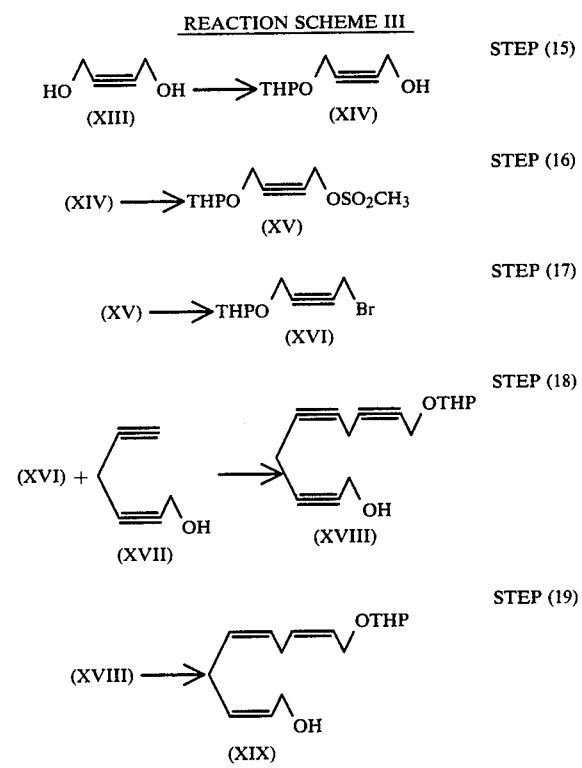

-continued
REACTION SCHEME III

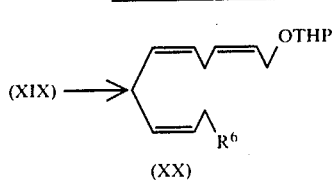

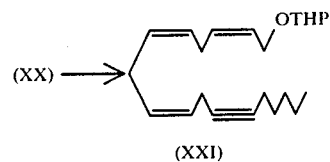

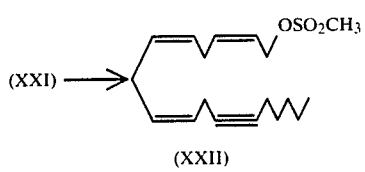

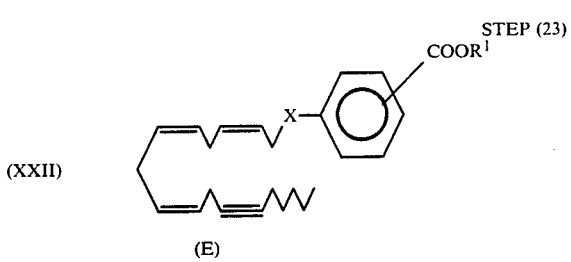

Wherein $R^1$, $R^6$ and X are as defined in Reaction Scheme 1 above.

In STEP (15) 2-butyne-1,4-diol (XIII), a commercially available compound is conventionally etherified with dihydropyran in the presence of an acid catalyst, such as p-toluenesulfonic acid, in a suitable inert solvent, e.g., tetrahydrofuran, to produce the mono-tetrahydropyranyl ether (XIV) and a small amount of the bis-tetrahydropyranyl ether. The latter compound can be selectively hydrolyzed to the monoetherified derivative by reacting it with pyridinium p-toluenesulfonate in ethanol solution, at a temperature of between 40° C. to 60° C., preferably at about 55° C., for between 1 to 3 hours.

In STEP (16) the monotetrahydropyranyl ether (XIV) is readily converted into the monotetrahydropyranyl ether mesylate (XV) by reaction with methanesulfonyl chloride in the presence of a tertiary amine, such as triethylamine, in an inert organic solvent, using preferably methylene chloride as solvent. The reaction is carried out at between −10° C. to 10° C., preferably at about 0° C., for between 20 minutes to 1 hour. Between 1.1 to 2 molar equivalents of methanesulfonyl chloride and triethylamine, preferably about 1.5 molar equivalents of each reagent, is used per mole of starting material.

In STEP (17) the crude mesylate (XV) is then treated with an excess of between 3 to 8 molar equivalents of an alkali metal bromide, preferably 5 molar equivalents of lithium bromide in acetone solution, at between 20° C. to 50° C. for a period of time between 30 minutes to 3 hours, 1-bromobut-2-yn-4-ol tetrahydropyranyl ether, compound (XVI), is produced by this reaction.

In STEP (18), 1-bromobut-2-yn-4-ol tetrahydropyranyl ether, (XVI) is coupled with hexa-2,5-diyn-1-ol (XVII) [D. Van der Steen et al, *Recueil*, 82, 1015 (1963)] via formation of its Grignard reagent, to produce the compound (XVIII) that is, deca-2,5,8-triyne-1,10-diol 10-monotetrahydropyranyl ether. The reaction conditions correspond to those employed in STEP (3) of REACTION SCHEME I.

In STEP (19) the triyne compound (XVIII) is then hydrogenated, preferably in the presence of Lindlar's catalyst partially deactivated by quinoline to produce the 2(Z),5(Z),8(Z)-triene (XIX). The hydrogenation conditions are those set forth above in STEP (1) of REACTION SCHEME I.

In STEP (20) the triene is in turn converted into a 1-halo derivative (XX) via esterification of the hydroxyl group with methanesulfonyl chloride, followed by treatment of the crude mesylate with an excess of an alkali metal halide, preferably sodium iodide in the presence of sodium bicarbonate. The reaction conditions and proportion of reagents are the same as previously described for STEPS (1) and (2), respectively.

In STEP (21) (XX) is then coupled with the Grignard reagent of 1-heptyne, using preferably about 3 moles of the alkyne per mole of compound (XX); the reaction conditions otherwise correspond to those mentioned above in STEP (3) to produce compound (XXIX).

In STEP (22) (XXI), that is, heptadeca-2(Z),5(Z),8(Z)-trien-11-yn-1-ol tetrahydropyranyl ether is then hydrolyzed with Pyr/PTS in ethanol solution. The free hydroxyl group is esterified with methanesulfonyl chloride in methylene chloride in the presence of triethylamine, to produce the mesylate (XXII), that is, heptadeca-2(Z),5(Z),8(Z)-trien-11-yn-1-ol methanesulfonate.

In STEP (23) (XXIII) is condensed with an alkyl ester of an o-, m- or p-mercaptobenzoic acid or an o-, m- or p-salicylic acid, preferably the methyl esters in the presence of sodium methoxide there are obtained the corresponding alkyl ester E where $R^1$ is alkyl. In general, the reaction conditions are those described in detail for STEPS (5) and (6), REACTION SCHEME I.

The esterified compounds are converted into the free acids compound E where $R^1$ is H by treatment with a base, for example, sodium hydroxide followed by acid treatment. The reaction conditions correspond in general to those described hereinbefore for STEP (8) of REACTION SCHEME I. The compounds and intermediates described herein can be isolated and purified, if desired, by any suitable separation or purification procedure. Examples include, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The free acids of the present invention encompassed by formula (A) can be converted into esters other than those obtained as intermediates by the esterification methods known in the art, preferably by treatment with an excess of a diazoalkane such as diazomethane, diazoethane, diazopropane and the like in ether solution.

Alternatively, the esters can be prepared through the sodium salt, which is in turn reacted with an alkyl halide, preferably an alkyl bromide. The sodium salt is conveniently obtained by treatment of the free acid with 1-1.1 molar equivalents of sodium methoxide or sodium carbonate in an inert organic solvent, preferably methanol, at room temperature. Thereafter the sodium salt is reacted with 1 to 1.1 molar equivalents of the desired alkyl halide for example, methyl bromide, isopropyl bromide, n-butyl bromide and the like in an inert organic solvent, preferably in dimethyl sulfoxide, at a temperature of from 0° C. to 35° C., preferably at room temperature, for about 2 to 6 hours. The pharmaceutically acceptable salts of the free acids of the present invention of formula (A), $R^1$ is H, are prepared by treatment of the acid compound with at least one molar equivalent of an inorganic or an organic base. Typical bases used as reagents include sodium hydroxide, potassium hydroxide, ammonium hydroxide, calcium hydroxide, diethylamine, tromethamine, lysine, caffeine, and the like. The reaction is conducted in water, alone or in combination with an inert, water-miscible organic solvent, at a temperature of from about 0° C., to about 50° C., preferably at room temperature. Typical water miscible organic solvents include methanol, ethanol, isopropanol, butanol, acetone, dioxane or tetrahydrofuran. The molar ratio of the free acid to base used are chosen to provide the ratio desired for any particular salt.

The compounds of the present invention, both intermediates and final products, are unstable and therefore it is convenient to store them at low temperature, preferably in dry ice.

Summary of Methods of Preparation

In summary, the compounds of this invention, formula (A) are prepared as follows:

compounds of formula (C), where X is S or O, are made by reacting formula (V) with the alkaline metal salt of either the phenol carboxylic acid or the thiophenol carboxylic acid;

compounds of formula (C), where X is $(CH_2)_n$, are made by reacting formula (III) with a benzoic acid ester derivative substituted at the ortho, meta or para position by an ω-alkynylalkyl radical of 4 to 7 carbon atoms in the presence of cuprous ions;

compounds of formula (D) can be made by reacting (XII) with the alkaline metal salt of either the phenol carboxylic acid or the thiophenol carboxylic acid;

compounds of formula (E) can be made by reacting (XXIII) with the alkaline metal salt of either the phenol carboxylic acid or the thiophenol carboxylic acid;

compounds of formula (F), where X is S or O, are made by reacting formula (VII) with the alkaline metal salt of either the phenol carboxylic acid or the thiophenol carboxylic acid; and compounds of formula (B) can be prepared by reacting a compound of formula (C), (D), (E), or (F) with molecular hydrogen in the presence of a catalytic metal in the presence of quinolin.

The acid form of the compounds of this invention can be made from the esters, the salts can be made from the acids, the acids from the salts, and the esters from the acids, all by conventional techniques.

EXAMPLES

Preparation 1

Pentadeca-2,5,8-triyn-1-ol tetrahydropyranyl ether

A.

80 g (0.57 mole) of propargyl alcohol tetrahydropyranyl ether was added to a suspension of lithium amide (prepared from 12.4 g of lithium and 0.1 g of ferric chloride as a catalyst) in 1.5 liter of liquid ammonia over 20 minutes. The resulting mixture stirred for an additional hour. Subsequently, a solution of 90 g (0.57 mole) of n-hexyl bromide in 100 ml of dry ether was slowly added. Stirring was continued for 18 hours, after which time the ammonia was allowed to evaporate, and 50 ml of saturated ammonium chloride solution were added; the mixture was then extracted with ether, the combined extracts washed with water, dried and the solvent removed. The residue was distilled at 102°–105° C./0.6 mm, thus obtaining 2-nonyn-1-ol tetrahydropyranyl ether.

B.

A solution of 40 g (0.178 mole) of 2-nonyn-1-ol-tetrahydropyranyl ether and 8 g (7.9 mmole) of Pyr/PTS in 150 ml of 96% ethanol was stirred at 60° C. for 3 hours. The solvent was evaporated under vacuum and the residue was partitioned between methylene chloride (120 ml) and water (120 ml). The organic phase was dried and evaporated. The residue was purified by column chromatography on 1.8 kg of silica gel, using hexane-ethyl acetate (95:5) as eluant, thus obtaining 2-nonyn-1-ol, as an oil.

C.

To a cooled (0° C.) solution of 14.6 g (0.104 mole) of 2-nonyn-1-ol in 150 ml of dry methylene chloride and 23.14 ml (0.166 mole) of triethylamine there were added dropwise 10.7 ml (0.156 mole) of methanesulfonyl chloride. The reaction mixture was stirred for 30 minutes at the same temperature, diluted with methylene chloride (150 ml), washed with brine (100 ml), dried and evaporated under vacuum to provide 2-nonyn-1-ol methanesulfonate.

D.

The crude mesylate (0.098 mole) was dissolved in 150 ml of acetone and the solution added to a mixture of 31 g (0.35 mole) of lithium bromide and 70 ml of acetone. The mixture was stirred at room temperature for 30 minutes; the solvent was then removed under vacuo, and the residue taken up in 300 ml of a (1:1) methylene chloride:water mixture. The organic layer was dried and evaporated to dryness. Purification by column chromatography on 300 g of silica gel, eluting with hexane, provided 1-bromo-2-nonyne.

E.

To a stirred solution of 10.8 g (60 mmole) of hexa-2,5-diyn-1-ol tetrahydropyranyl ether [D. Van der Steen et al, *Recueil* 82, 1015 (1963)] in 100 ml of dry tetrahydrofuran there were added dropwise, under argon atmosphere, at 0°–5° C. 16.9 ml (0.60 mmol) of a 3.5N ethylmagnesium bromide solution in ether, maintaining the temperature at 0°–5° C. The mixture was stirred for 2 hours at 10°–15° C. and then 0.1 g of cuprous chloride were added. After 15 minutes a solution of 5.35 g (26 mmole) of 1-bromo-2-nonyne in 60 ml of dry tetrahydrofuran was added dropwise and the mixture stirred at room temperature for 3 hours. The reaction mixture was diluted with 70 ml of saturated ammonium chloride solution and extracted with methylene chloride. The organic extracts were dried and evaporated, and the residue purified by column chromatography on 450 g of silica gel, using hexane-ethyl acetate (99:1) as eluant, to provide pentadeca-2,5,8-triyn-1-ol tetrahydropyranyl ether.

Preparation 2

10-Phenoxydeca-2,5,8-triyn-1-ol tetrahydropyranyl ether

A.

To a solution of 90 g (1.07 mol) of 2-butyne-1,4-diol and 9 g of p-toluenesulfonic acid in 1000 ml of tetrahydrofuran, cooled to 0° C., there were added dropwise 104.88 ml (96.69 g, 1.15 mol) of dihydropyran, and thereafter the reaction mixture was stirred for 3 hours at room temperature. It was then neutralized with triethylamine and evaporated in vacuo. The residue was purified by silica gel column chromatography (2000 g) using hexane-ethyl acetate (80:20) as eluant, to yield 2-butyne-1,4-diol monotetrahydropyranyl ether and a small amount of the bis-tetrahydropuranyl ether.

B.

To a solution of 15 g (0.088 mol) of the foregoing monotetrahydropyranyl ether and 19.79 ml (14.25 g, 0.141 mol) of triethylamine in 250 ml of anhydrous methylene chloride, there were added dropwise 10.24 ml (15.15 g, 0.1323 mol) of methanesulfonyl chloride, at such a rate to maintain the reaction temperature at 0° C., stirring the reaction mixture for 30 minute further at 0° C. It was then poured into aqueous saturated sodium bicarbonate solution and extracted with methylene chloride. The combined organic extracts were dried and evaporated, to yield 4-tetrahydropyranyloxybut-2-yn-1-ol methanesulfonate, in almost quantitative yield. This crude product was dissolved in 50 ml of acetone and treated with a solution of 40.34 g (0.4636 mol) of lithium bromide in 200 ml of acetone, stirring the reaction mixture at room temperature for 1 hour. The solvent was then evaporated and the residue diluted with water and extracted with methylene chloride, the organic extracts were dried and evaporated in vacuo. The crude material was purified by silica gel column chromatography using hexane-ethyl acetate (95:5) as eluant, to yield 1-bromobut-2-yn-4-ol-tetrahydropyranyl ether, as an oil.

C.

To a solution of 2.35 g (0.025 mol) of phenol in 20 ml of absolute ethanol, there was added 1.10 g (0.0275 mol) of sodium hydroxide. The mixture was refluxed until complete disolution and 2.92 g (0.0125 mol) of 1-bromobut-2-yn-4-ol tetrahydropyranyl ether were added, and the reflux resumed for 2 additional hours. It was then cooled, poured into water and extracted with ether. The organic extracts were washed with 20% aqueous sodium hydroxide solution and water, dried and evaporated in vacuo. The residue was purified by column chromatography on 50 g of silica gel, using hexane-ethyl acetate (98:2) as eluant, to yield 4-phenoxybut-2-yn-1-ol tetrahydropyranyl ether, as an oil.

D.

To a solution of 2 g (0.008 mol) of 4-phenoxybut-2-yn-1-ol tetrahydropyranyl ether in 20 ml of 96% ethanol, there was added 1.02 g (0.004 mol) of Pyr/PTS. The reaction mixture was stirred for 2 hours at 55° C.; the solvent was then removed in vacuo and the residue diluted with 20 ml of water and extracted with methylene chloride. The combined extracts were dried and evaporated in vacuo. The residue was purified by column chromatography on 30 g of silica gel, using hexane-ethyl acetate (90:10) as eluant, to yield 4-phenoxybut-2-yn-1-ol, as an oil.

E.

By following the esterification method of part B of this preparation, the preceding compound was converted into 4-phenoxybut-2-yn-1-ol methanesulfonate in almost quantitative yield. The foregoing crude mesylate was dissolved in 15 ml of acetone and treated with a solution of 5.55 g (0.037 mol) of sodium iodide and 1.049 g (0.0123 mol) of sodium bicarbonate in 30 ml of acetone. The reaction mixture was stirred for 1 hour at room temperature and then the solvent was removed under reduced pressure. The residue was diluted with water and extracted with methylene chloride; the organic extracts were dried and evaporated. The residue was purified by silica gel column chromatography using hexane-ethyl acetate (95:5) as eluant, to yield 1-iodo-4-phenoxybut-2-yne.

F.

To a cold (−20° C.) solution of 2.879 g (0.0161 mol) of hexa-2,5-diyn-1-ol tetrahydropyranyl ether [D. Van der Steen et al, Recueil 82, 1015 (1963)] in 30 ml of tetrahydrofuran, there were added dropwise, under argon atmosphere, 4.0 ml (2.15 g, 0.016 mol) of a 4.05N solution of ethylmagnesium bromide in ether, maintaining the temperature at −20° C. After the addition was finished, the reaction mixture was stirred for 2 hours further at −20° C. Then, 52.8 mg (0.53 mmol) of cuprous chloride was added. The mixture was stirred for 20 additional minutes, warmed to room temperature and 2.2 g (0.008 mol) of 1-iodo-4-phenoxybut-2-yne were added. The reaction mixture was then stirred at room temperature for 3 hours, poured into 50 ml of saturated ammonium chloride solution and extracted with ether. The combined extracts were dried and evaporated in vacuo. The residue was purified by column chromatography on 80 g of silica gel, using hexane-ether (90:10) as eluant, thus obtaining 10-phenoxydeca-2,5,8-triyn-1-ol tetrahydropyranyl ether, as an oil.

Similarly, using the following compounds instead of phenol in part C of the preparation above;
p-methylphenol,
m-methoxyphenol,
m-fluorophenol,
o-bromophenol,
p-butylphenol,
m-trifluoromethylphenol and
p-cyanophenol
there are respectively obtained as final products:
10-(p-methylphenoxy)deca-2,5,8-triyn-1-ol tetrahydropyranyl ether;
10-(m-methoxyphenoxy)deca-2,5,8-triyn-1-ol tetrahydropyranyl ether;
10-(m-fluorophenoxy)deca-2,5,8-triyn-1-ol tetrahydropyranyl ether;
10-(o-bromophenoxy)deca-2,5,8-triyn-1-ol tetrahydropyranyl ether;
10-(p-butylphenoxy)deca-2,5,8-triyn-1-ol tetrahydropyranyl ether;
10-(m-trifluoromethylphenoxy)deca-2,5,8-triyn-1-ol tetrahydropyranyl ether; and
10-(p-cyanophenoxy)deca-2,5,8-1-ol tetrahydropyranyl ether.

Preparation 3

10-Phenylthiodeca-2,5,8-triyn-1-ol tetrahydropyranyl ether

A stirred solution of sodium ethoxide in ethanol, obtained from 1.3 g of sodium and 50 ml of absolute ethanol was treated dropwise with 5.5 g (0.05 mol) of thiophenol in 15 ml of absolute ethanol. The reaction mixture was refluxed for 1 hour and then treated with 5.84 g (0.025 mol) of 1-bromobut-2-yn-4-ol tetrahydropyranyl ether, refluxing the mixture for 2 additional hours. It was then cooled, poured into water and extracted with methylene chloride. The organic extract was washed with water, dried and evaporated to dryness in vacuo. The residue was purified by silica gel column chromatography, to produce 4-phenylthiobut-2-yn-1-ol tetrahydropyranyl ether, as an oil.

The above compound was then submitted to the procedures of Preparation 2, parts D, E and F, to produce 10-phenylthiodeca-2,5,8-triyn-1-ol tetrahydropyranyl ether as final product. Similarly, substituting p-thiocresol for thiophenol 10-(p-methylphenylthio)-deca-2,5,8-triyn-1-ol tetrahydropyranyl ether can be obtained.

Preparation 4

2-(3-n-butynyl)benzoic acid methyl ester

A.

A stirred mixture of 19.67 ml (14.16 g, 0.14 mol) of diisopropylamine and 50 ml of anhydrous tetrahydrofuran, cooled to −10° C. was treated dropwise with 94.92 ml (9 g, 0.14 mol) of a 1.47N solution of n-butyl lithium, under argon atmosphere. After 30 minutes at 0° C., a solution of 9.52 g (0.07 mol) of o-toluic acid in 20 ml of anhydrous tetrahydrofuran was added; the mixture was stirred for 30 additional minutes at 0° C. and then treated with 12.11 ml (17.0 g, 0.14 mol) of allyl bromide in 20 ml of anhydrous tetrahydrofuran. The resulting mixture was stirred at 0° C. for 1 hour further, diluted with water and extracted with ether. The extract was dried and evaporated to dryness and the residue treated with ethereal diazomethane until the color of the reagent persisted in the mixture. The solvent and excess reagent were eliminated under vacuo and the residue distilled at 130°–136° C./20 mm, thus obtaining 2-(3-n-butenyl)benzoic acid methyl ester.

B.

A stirred solution of 1.3 g of the foregoing compound in 10 ml of anhydrous chloroform, cooled to 0° C. was treated dropwise with 0.412 ml of bromine dissolved in 5 ml of chloroform, stirring the mixture for 1 hour further at 0° C. The solvent was eliminated under vacuo, the residue taken up in 15 ml of absolute ethanol and treated with 1.91 g of potassium hydroxide, refluxing the mixture for 30 hours. The solvent was then eliminated, and the residue diluted with water and acidified with 10% hydrochloric acid. The product was extracted with methylene chloride, and the extract dried and evaporated. The residue was esterified with an excess of ethereal diazomethane as described previously and the product purified by thin layer chromatography using hexane-benzene (1:1) as gradient, thus obtaining the title compound, as an oil.

In a similar manner, substituting allyl bromide with 1-bromo-3-butene and 1-bromo-4-pentene 2(4-n-pentynyl)benzoic acid and 2(5-n-hexynyl)benzoic acid can be obtained.

EXAMPLE 1

Heptadeca-5(Z), 8(Z), 11(Z)-trien-2-yn-1-ol tetrahydropyranyl ether

A.

Tetradeca-2(Z),5(Z),8(Z)-trien-1-ol tetrahydropyranyl ether

A solution of 9.5 g (33 mol) of tetradeca-2,5,8-triyn-1-ol tetrahydropyranyl ether [D. Van der Steen et al, *Recueil* 82, 1015 (1963)] in 100 ml of absolute methanol was hydrogenated at room temperature and atmospheric pressure in the presence of 0.65 g of Lindlar's catalyst and 0.2 ml of quinoline, until absorption of 3 molar equivalents of hydrogen. The catalyst was then separated by filtration through celite and the filtrate evaporated in vacuo. Purification of the residue by column chromatography on 300 g of silica gel using hexane-methylene chloride (95:5) as eluant afforded the title compound, as an oil.

B.

Tetradeca-2(Z),5(Z),8(Z)-trien-1-ol

A solution of 7.65 g (26.1 mmol) of tetradeca-2(Z),5(Z),8(Z)-trien-1-ol tetrahydropyranyl ether in 150 ml of ethanol and 0.65 g (2.6 mmol) of Pyr/PTS was immersed in a preheated oil bath, at 60° C. After 2 hours, the solvent was removed under vacuo and the residue extracted with methylene chloride (3×100 ml). The combined extracts were washed with brine (60 ml), dried over magnesium sulfate and evaporated to dryness under vacuo. The residue was purified by column chromatography on 300 g of silica gel using hexane-ethyl acetate (90:10) as eluant, thus obtaining the title compound, as an oil.

C.

Tetradeca-2(Z),5(Z),8(Z)-trien-1-ol methanesulfonate

A solution of 3.95 g (18 mmol) of tetradeca-2(Z),5(Z),8(Z)-trien-1-ol in 60 ml of dry methylene chloride was cooled to 0° C. and 3.25 ml (23.4 mmol) of triethylamine and 1.67 ml (21.6 mmol) of methanesulfonyl chloride were added. The reaction mixture was stirred for 30 minutes at 0° C., diluted with 60 ml of methylene chloride, washed with 40 ml of brine, dried and evaporated under vacuum, to provide the methanesulfonate, which was used in the next step without further purification.

D.

1-Bromotetradeca-2(Z),5(Z),8(Z)-triene

The crude mesylate (4.8 g, 16.75 mmol) was dissolved in 60 ml of acetone and the solution added to a mixture of 10 g (115 mmol) of lithium bromide and 60 ml of acetone. The mixture was stirred at room temperature for 45 minutes, the solvent was then removed under vacuum and the residue taken up in 80 ml of methylene chloride. The organic extract was washed with water, dried and evaporated to dryness. Purification by silica-gel column chromatography (120 g) using hexane as eluant gave the title compound in pure form, as an oil.

E.

Heptadeca-5(Z),8(Z),11(Z)-trien-2-yn-1-ol tetrahydropyranyl ether

To a stirred solution of 5.18 g (0.036 mol) of propargyl alcohol tetrahydropyranyl ether in 100 ml of dry tetrahydrofuran there were added dropwise, under argon atmosphere, 8.87 ml (0.036 mole) of a 4.05N solution of ethylmagnesium bromide, maintaining the temperature at 0°–5° C. The mixture was heated to reflux for 1 hour; cooled to room temperature and treated with 135 mg of cuprous chloride. The reaction mixture was stirred for 15 minutes further at the same temperature and then a solution of 5 g (0.018 mole) of 1-bromotetradeca-2(Z),5(Z),8(Z)-triene in 60 ml of tetrahydrofuran was added in a dropwise fashion. The mixture was refluxed for 3 hours, cooled to room temperature, and diluted with 15 ml of saturated ammonium chloride solution. The solid material was separated by filtration and washed with ether. The organic phase of the filtrate was dried and evaporated. Purification of the residue by thin layer chromatography using hexane-ethyl acetate (90:10) as gradient provided of the title compound, as an oil.

EXAMPLE 2

2-(Heptadeca-5'(Z),8'(Z),11'(Z)-trien-2'-ynylthio)benzoic acid

A.

Heptadeca-5(Z),8(Z),11(Z)-trien-2-yn-1-ol

A mixture of 1.6 g (4.8 mmol) of heptadeca-5(Z),8(Z),11(Z)-trien-2-yn-1-ol tetrahydropyranyl ether in 50 ml of 96% ethanol and 120 mg (0.48 mmol) of Pyr/PTS was placed in a preheated oil bath at 60° C. for 2 hours. The solvent was removed under vacuum and the residue was dissolved in 40 ml of methylene chloride, washed with 20 ml of brine, dried and evaporated. The product was purified by column chromatography on 60 g of silica gel, using hexane-ethyl acetate (95:5) as eluant, to provide the title compound, as an oil.

B.

Heptadeca-5(Z),8(Z),11(Z)-trien-2-yn-1-ol methanesulfonate

By following the method of part C of Example 1, 350 mg (1.4 mmol) of heptadeca-5(Z),8(Z),11(Z)-trien-2-yn-1-ol in 10 ml of anhydrous methylene chloride was esterified with 0.12 ml (1.68 mmol) of methanesulfonyl chloride in the presence of 0.25 ml (1.82 mmol) of triethylamine, to produce the title compound, which was used in the next step without further purification.

C.

2-(Heptadeca-5'(Z),8'(Z),11'(Z)-trien-2'-ynylthio)benzoic acid methyl ester

A solution of 51 mg (2.2 m atoms) of sodium metal in 4 ml of absolute methanol was cooled to 0° C. and 190 mg (1.11 mmol) of methyl thiosalicylate were added; after stirring at room temperature for 5 minutes there was added a solution of 280 mg (0.86 mmol) of the crude mesylate in 4 ml of absolute methanol, following the course of the reaction by t.l.c. After 30 minutes at room temperature the mixture was diluted with 6 ml of water, acidified with 10% hydrochloric acid solution and extracted with methylene chloride (3×8 ml). The combined extracts were washed with brine (6 ml), dried and evaporated under vacuum. The residue was purified by thin layer chromatography using hexane-ethyl acetate (97:3) as gradient (2 developments), to produce the title compound, as an oil.

U.V.: $\lambda max^{MeOH}$ 232, 261, 320 nm ($\epsilon$ 13800, 7244, 2630).

I.R.: (CHCl$_3$) 1720, 1595 cm$^{-1}$.

N.M.R.: (CDCl$_3$) 0.9 (t, 3H); 1.33 (m, 6H); 2.06 (m, 2H); 2.56–3.0 (m, 6H); 3.66 (t, 2H); 3.93 (s, 3H); 5.36 (m, 6H); 7.0–8.16 (m, 4H).

M.S.: 396 (M+).

D.

2-(Heptadeca-5'(Z),8'(Z),11'(Z)-trien-2'-ynylthio)benzoic acid

A solution of 230 mg (0.58 mmol) of 2-(heptadeca-5'(Z),8'(Z),11'(Z)-trien-2'-ynylthio)benzoic acid methyl ester in 6 ml of a 0.5N methanolic sodium hydroxide solution was stirred at room temperature for 64 hours, 8 ml of water were then added and thereafter the mixture was acidified with 10% hydrochloric acid. The product was extracted with methylene chloride (3×10 ml) and the combined extracts dried and evaporated in vacuo. The product was purified by column chromatography on 10 g of silica gel, using methylene chloride as eluant, to afford the title compound, as an oil.

U.V.: $\lambda max^{MeOH}$ 231, 261, 320 nm ($\epsilon$ 12300, 7079, 2818).

I.R.: (CHCl$_3$) 3550, 1695, 1585 cm$^{-1}$.

N.M.R.: (CDCl$_3$) 0.86 (t, 3H); 1.33 (m, 6H); 2.06 (m, 2H); 2.56–3.0 (m, 6H); 3.66 (s, 2H); 5.43 (m, 6H); 7.06–8.26 (m, 4H); 8.5–9.16 (m, 1H COO$\underline{H}$).

M.S.: 382 (M+).

EXAMPLE 3

3-(Heptadeca-5'(Z),8'(Z),11'(Z)-trien-2'-ynylthio)benzoic acid

A.

3-(Heptadeca-5'(Z),8'(Z),11'(Z)-trien-2'-ynylthio)benzoic acid methyl ester

To a solution of sodium methoxide, prepared from 51 mg (2.2 m atoms) of sodium and 3 ml of methanol, cooled to 0° C., there were added 199 mg (1.18 mmol) of methyl m-mercaptobenzoate and 285 mg (0.986 mmol) of heptadeca-5(Z),8(Z),11(Z)-trien-2-yn-1-ol methanesulfonate dissolved in 6 ml of absolute methanol. The mixture was stirred at room temperature for 30 minutes, 10 ml of water were added, followed by acidification with saturated oxalic acid solution; the product was extracted with methylene chloride (3×15 ml), and the combined extracts dried over magnesium sulfate and evaporated. The residue was purified by thin layer chromatography using hexane-ethyl acetate (93:7) as gradient, thus obtaining the title compound, as an oil.

U.V.: $\lambda max^{MeOH}$ 225, 257, 307 nm ($\epsilon$ 17780, 5248, 831).

I.R.: (CHCl$_3$) 1725, 1580 cm$^{-1}$.

N.M.R.: (CDCl$_3$) 0.93 (t, 3H); 1.36 (m, 6H); 2.13 (m, 2H); 2.66–3.06 (m, 6H); 3.66 (t, 2H); 3.96 (s, 3H, COOCH$_3$); 5.23–5.56 (m, 6H); 7.2–8.16 (m, 4H).

M.S.: 396 (M+).

B.

3-(Heptadeca-5'(Z),8'(Z),11'(Z)-trien-2'-ynylthio)benzoic acid

A solution of 280 mg (0.70 mmol) of 3-(heptadeca-5'(Z),8'(Z),11'(Z)-trien-2'-ynylthio)benzoic acid methyl ester in 6 ml of 0.5N methanolic sodium hydroxide solution was stirred at room temperature for 62 hours. The mixture was then diluted with 8 ml of water, acidified with saturated oxalic acid solution and extracted with methylene chloride (3×10 ml). The combined extracts were dried and evaporated in vacuo. The residue was purified by column chromatography on 10 g of silica gel, using methylene chloride as eluant, thus obtaining the title compound, as an oil.

U.V.: $\lambda max^{MeOH}$ 207, 223, 258, 296, 308, 320 nm ($\epsilon$ 28840, 19950, 6166, 3311, 3802, 2884).

I.R.: (CHCl$_3$) 3520, 1700, 1600 cm$^{-1}$.

N.M.R.: (CDCl$_3$) 0.86 (t, 3H); 1.26 (m, 6H); 2.06 (m, 2H); 2.63–3.06 (m, 6H); 3.66 (t, 2H); 5.2–5.53 (m, 6H); 7.16–8.16 (m, 4H).

M.S.: 383 (MH+).

EXAMPLE 4

4-(Heptadeca-5'(Z),8'(Z),11'(Z)-trien-2-ynylthio)benzoic acid

Example 3 was repeated using in part A, 205 mg (0.63 mmol) of heptadeca-5(Z),8(Z),11(Z)-trien-2-yn-1-ol methanesulfonate as starting material, 57 mg (2.5 m atoms) of sodium, 9 ml of methanol and 140 mg (0.81 mmol) of methyl p-mercaptobenzoate in place of the m-isomer. There were obtained 4-(heptadeca-5'(Z),8'(Z),11'(Z)-trien-2-ynylthio)benzoic acid methyl ester, as an oil.

U.V.: $\lambda max^{MeOH}$ 226, 290 nm ($\epsilon$ 9120, 16600).

I.R.: (CHCl$_3$) 1720, 1600 cm$^{-1}$.

N.M.R.: (CDCl$_3$) 0.86 (t, 3H); 1.3 (m, 6H); 2.06 (m, 2H); 2.6–3.06 (m, 6H); 3.66 (t, 2H); 3.9 (s, 3H, —COOCH$_3$); 5.16–5.6 (m, 6H); 7.4 (d, 2H); 8.0 (d, 2H).

M.S.: 396 (M+).

Upon hydrolysis of 160 mg (0.4 mmol) of the foregoing methyl ester with 0.5N methanolic sodium hydroxide, as described in part B of Example 3, there were obtained 4-(heptadeca-5'(Z),8'(Z),11'(Z)-trien-2-ynylthio)benzoic acid in pure form, as a solid with a low melting point.

U.V.: $\lambda max^{MeOH}$ 225, 283 nm ($\epsilon$ 8913, 13490).

I.R.: (CHCl$_3$) 3300, 1700, 1600 cm$^{-1}$.

N.M.R.: (CDCl$_3$) 0.9 (t, 3H); 1.33 (m, 6H); 2.06 (m, 2H); 2.6–3.06 (m, 6H); 3.7 (t, 2H); 5.16–5.7 (m, 6H); 7.4 (d, 2H); 8.06 (d, 2H); 8.43–9.13 (m, 1H,COO$\underline{H}$).

M.S.: 382 (M+).

EXAMPLE 5

Phenyl (heptadeca-5(Z),8(Z),11(Z)-trien-2-ynyl) thioether

A solution of 21 mg (0.91 m atoms) of sodium in 3 ml of absolute methanol was cooled to 0° C. and then 50 mg (0.45 mmol) of thio-phenol, followed by a solution of 115 mg (0.35 mmol) of heptadeca-(Z),8(Z),11(Z)-trien-2-yn-1-ol methanesulfonate in 3 ml of absolute methanol were added. The reaction mixture was stirred at room temperature for 30 minutes, diluted with 8 ml of water and neutralized with 10% hydrochloric acid. The product was extracted with methylene chloride (3×10 ml), the extracts were dried and evaporated under reduced pressure. The residue was purified by thin layer chromatography, using hexane as gradient (3 developments), thus obtaining the title compound, as an oil.

U.V.: $\lambda max^{McOH}$ 253 nm ($\epsilon$ 5012).
I.R.: (CHCl$_3$) 1575 cm$^{-1}$.
N.M.R.: (CDCl$_3$) 0.9 (t, 3H); 1.3 (m, 6H); 2.0 (m, 2H); 2.56–3.0 (m, 6H); 3.63 (s, 2H); 5.13–5.63 (m, 6H); 7.13–7.56 (m, 5H).
M.S.: 338 (M+).

EXAMPLE 6

2-(Heptadeca-2'(Z),5'(Z),8'(Z),11'(Z)-tetraenylthio)-benzoic acid

A.

Heptadeca-2(Z),5(Z),8(Z),11(Z)-tetraen-1-ol-tetrahydropyranyl ether

A solution of 1.3 g (3.9 mmol) of heptadeca-5(Z),8(Z),11(Z)-trien-2-yn-1-ol tetrahydropyranyl ether in 60 ml of absolute methanol was hydrogenated at room temperature in the presence of 130 mg of pre-reduced Lindlar's catalyst and 0.2 ml of quinoline, until the stoichiometric amount of hydrogen was consumed. The catalyst was separated by filtration through celite and the filtrate concentrated in vacuo. Purification of the residue by silica gel column chromatography, using hexane-ethyl acetate (98:2) as eluant, gave the title compound, as an oil.

B.

Heptadeca-2(Z),5(Z),8(Z),11(Z)-tetraen-1-ol

A solution of 1.1 g (3.3 mmol) of the foregoing tetrahydropyranyl ether and 83 mg (0.33 mmol) of Pyr/PTS in 30 ml of ethanol was stirred at 55° C. for 3 hours. The solvent was evaporated in vacuo and the residue chromatographed on a 40 g silica gel column, using hexane-ethyl acetate (97:3) as eluant, to afford the title compound, as an oil.

C.

Heptadeca-2(Z),5(Z),8(Z),11(Z)-tetraen-1-ol methanesulfonate

In accordance with the method of Example 1, part C, 120 mg of the hydroxy compound obtained in part B of this Example in 4 ml of dry methylene chloride and 0.086 ml of thiethylamine were esterified with 0.044 ml (0.57 mmol) of methanesulfonyl chloride, obtaining the title mesylate.

D.

2-Heptadeca-2'(Z),5'(Z),8'(Z),11'(Z)-tetraenylthio)benzoic acid methyl ester

To a cooled (0° C.) solution of 27 mg (1.17 m atoms) of sodium in 4 ml of absolute methanol there were added 78 mg (0.47 mmol) of methyl thiosalicylate. After stirring 5 minutes, a solution of 128 mg (0.39 mmol) of the foregoing mesylate in 3 ml of methanol was added. The reaction mixture was stirred at room temperature for 1 hour, diluted with 5 ml of water, acidified with 10% hydrochloric acid, and extracted with methylene chloride (3×6 ml). The combined extracts were washed with brine (5 ml), dried and evaporated in vacuo. The residue was purified by thin layer chromatography, using hexane-ethyl acetate (95:5) as gradient, to afford the title compound, as an oil.

U.V.: $\lambda_{max}^{MeOH}$ 233, 263, 320 nm ($\epsilon$9120, 6166, 2840).
I.R.: (CHCl$_3$) 1715, 1585 cm$^{-1}$.
N.M.R.: (CDCl$_3$) 0.86 (t, 3H); 1.3 (m, 6H); 2.06 (m, 2H); 2.6–3.1 (m, 6H); 3.6 (m, 2H); 3.9 (s, 3H, COOC$\underline{H}_3$); 5.2–5.8 (m, 8H); 7.06–8.13 (m, 4H).

E.

2-(Heptadeca-2'(Z),5'(Z),8'(Z),11'(Z)-tetraenylthio)-benzoic acid

A solution of 65 mg (0.16 mmol) of 2-(heptadeca-2'(Z),5'(Z),8'(Z),11'(Z)-tetraenylthio)benzoic acid methyl ester in 2 ml of methanol was treated with 2 ml of a 0.5N solution of sodium hydroxide, in methanol stirring the mixture at room temperature during 20 hours. It was then diluted with 5 ml of water, acidified with 10% hydrochloric acid and extracted with methylene chloride (3×5 ml); the combined extracts were dried and evaporated under vacuum. Purification of the crude product by column chromatography on 3 g. of silica gel, using methylene chloride as eluant, gave the title compound, as an oil.

U.V.: $\lambda_{max}^{MeOH}$ 233, 263, 319 nm ($\epsilon$9550, 7244, 2630).
I.R.: (CHCl$_3$) 3250, 1695, 1590 cm$^{-1}$.
N.M.R.: (CDCl$_3$) 0.86 (t, 3H); 1.26 (m, 6H); 2.03 (m, 2H); 2.8 (m, 6H); 3.6 (m, 2H); 5.16–5.73 (m, 8H); 7.06–8.23 (m, 4H); 9.6–10.5 (m, 1H, COO$\underline{H}$).
M.S.: 385 (MH+).

Similarly starting with eicosa, 8(Z), 11(Z), 14(Z)-trien-2-yn-1-ol the tetrahychopyranyl ether, in place of heptadeca-5(Z), 8(Z), 11(Z)-triene-Z-yn-1-ol in Step A of the above procedure, and following the subsequent steps 2-(eicosa-5'(Z); 8'(Z), 11'(Z), 14'(Z)-tetra enylthio)benzoic can be made.

EXAMPLE 7

3-(Heptadeca-2'(Z),5'(Z),8'(Z),11'(Z)-tetraenylthio)-benzoic acid

To a solution of 57 mg (2.5 m atoms) of sodium in 4 ml of absolute methanol cooled to 0° C., there were added 218 mg (1.29 mmol) of methyl m-mercaptobenzoate. After stirring 5 minutes, a solution of 325 mg (0.995 mmol) of heptadeca-2(Z),5(Z),8(Z),11(Z)-tetraen-1-ol methanesulfonate in 8 ml of absolute methanol was added. After 40 minutes, the reaction mixture was diluted with water, acidified with saturated oxalic acid solution and extracted with methylene chloride (3×10 ml). The organic extracts were dried and concentrated under vacuum. The residue was purified by thin layer chromatography, using hexane-ethyl acetate (93:7) as gradient, to yield 3-(heptadeca-2'(Z),5'(Z),8'(Z),11'(Z)-tetraenylthio)benzoic acid methyl ester, as an oil.

U.V.: $\lambda_{max}^{MeOH}$ 209, 260, 308 nm ($\epsilon$ 25700, 6026, 1000).
I.R.: (CHCl$_3$) 1720, 1580 cm$^{-1}$.
N.M.R.: (CDCl$_3$) 0.86 (t, 3H); 1.33 (m, 6H); 2.06 (m, 2H); 2.8 (t, 2H); 3.6 (d, 2H); 3.9 (s, 3H); 5.1–5.66 (m, 8H); 7.13–8.16 (m, 4H).
M.S.: 398 (M+).

Upon hydrolysis of 290 mg of the preceding methyl ester with 0.5N sodium hydroxide in methanol, by the method of Example 3, there were obtained the title compound, as an oil.

U.V.: $\lambda_{max}^{MeOH}$ 208, 260, 305 nm ($\epsilon$ 30900, 6310, 1023).
I.R.: (CHCl$_3$) 3550, 1700, 1600, 1580 cm$^{-1}$.
N.M.R.: (CDCl$_3$) 0.9 (t, 3H); 1.33 (m, 6H); 2.06 (m, 2H); 2.8 (t, 6H); 3.6 (d, 2H); 5.13–5.66 (m, 8H); 7.2–8.16 (m, 4H); 8.8–9.5 (m, 1H, COO$\underline{H}$).

M.S.: 384 (M+).

EXAMPLE 8

4-(Heptadeca-2'(Z),5'(Z),8'(Z),11'(Z)-tetraenylthio)-benzoic acid

This compound was prepared in accordance with the method of Example 7, substituting in part A, methyl p-mercaptobenzoate for the corresponding m-isomer.

The following reagent quantities were used:

Sodium 57 mg (2.5 m atoms) in 4 l ml of absolute methanol methyl p-mercaptobenzoate 218 mg (1.29 mmol)

Heptadeca-2(Z),5(Z),8(Z),11(Z)-tetraen-1-ol methanesulfonate 325 mg (0.995 mole) in 5 ml of absolute methanol.

There were obtained 4-(heptadeca-2'(Z),5'(Z),8'(Z),11'(Z)-tetraenylthio)benzoic acid methyl ester, as an oil.

U.V.: $\lambda_{max}^{MeOH}$ 208, 225, 293 nm ($\epsilon$ 20890, 10470, 17380).

I.R.: (CHCl$_3$) 1725, 1600 cm$^{-1}$.

N.M.R.: (CDCl$_3$) 0.9 (t, 3H); 1.33 (m, 6H); 2.1 (m, 2H); 2.8 (m, 6H); 3.66 (d, 2H); 3.93 (s, 3H, COOC$\underline{H}_3$); 5.2–5.7 (m, 8H); 7.33 (d, 2H); 7.96 (d, 2H).

M.S.: 398 (M+).

The methyl ester group was hydrolyzed with 0.5N methanolic sodium hydroxide. From 255 mg of the esterified compound there were obtained the title free acid, as an oil.

U.V.: $\lambda_{max}^{MeOH}$ 208, 288 nm ($\epsilon$ 21880, 15140).

I.R.: (CHCl$_3$) 3520, 1695, 1595 cm$^{-1}$.

N.M.R.: (CDCl$_3$) 0.86 (t, 3H); 1.3 (m, 6H); 2.03 (m, 2H); 2.8 (t, 6H); 3.66 (d, 2H); 5.2–5.66 (m, 8H); 7.33 (d, 2H); 8.0 (d, 2H); 9.16–10.0 (m, 1H, COO$\underline{H}$).

M.S.: 385 (MH+).

EXAMPLE 9

2-(Octadeca-5'(Z),8'(Z),11'(Z)-trien-2-ynylthio)benzoic acid

By following the methods of Example 1, parts A through E and Example 2, parts A through C, using pentadeca-2,5,8-triyn-1-ol tetrahydropyranyl ether as starting material:

pentadeca-2(Z),5(Z),8(Z)-trien-1-ol tetrahydropyranyl ether;
pentadeca-2(Z),5(Z),8(Z)-trien-1-ol;
pentadeca-2(Z),5(Z),8(Z)-trien-1-ol methanesulfonate;
1-bromopentadeca-2(Z),5(Z),8(Z)-triene;
octadeca-5(Z),8(Z),11(Z)-trien-2-yn-1-ol tetrahydropyranyl ether;
octadeca-5(Z),8(Z),11(Z)-trien-2-yn-1-ol;
octadeca-5(Z),8(Z),11(Z)-trien-2-yn-1-ol methanesulfonate can be obtained.

2-(octadeca-5'(Z),8'(Z),11'(Z)-trien-2'-ynylthio)benzoic acid methyl ester, an oil, has the following constants:

U.V.: $\lambda_{max}^{MeOH}$ 223, 260, 296, 308, 321 nm ($\epsilon$ 19500, 9772, 5248, 7079, 6310).

I.R.: (CHCl$_3$) 3500, 1700, 1595 cm$^{-1}$.

N.M.R.: (CDCl$_3$) 0.9 (t, 3H); 1.33 (m, 8H); 2.06 (m, 2H); 2.6–3.1 (m, 6H); 3.66 (t, 2H); 5.4 (m, 6H); 7.3–8.26 (m, 5H).

M.S.: 363 (MH+).

Upon hydrolysis of the methyl ester group with 0.5N methanolic sodium hydroxide solution, in accordance with the method of Example 2, part D, there was obtained the title compound, as an oil.

U.V.: $\lambda_{max}^{MeOH}$ 224, 260, 315 nm ($\epsilon$ 19950, 7586, 3162).

I.R.: (CHCl$_3$) 1715, 1695 cm$^{-1}$.

N.M.R.: (CDCl$_3$) 0.9 (t, 3H); 1.33 (m, 8H); 2.06 (m, 2H); 2.63–2.73 (m, 6H); 3.66 (t, 2H); 3.93 (s, 3H, COOC$\underline{H}_3$); 5.4 (m, 6H); 7.06–8.16 (m, 4H).

M.S.: 410 (M+).

EXAMPLE 10

2-(13'-Phenoxytrideca-5'(Z),8'(Z),11'(Z)-trien-2'-ynylthio)benzoic acid

By following the method of Example 1, parts A, B and C, 10-phenoxydeca-2,5,8-triyn-1-ol tetrahydropyranyl ether can be converted successively into:

10-phenoxydeca-2(Z),5(Z),8(Z)-trien-1-ol tetrahydropyranyl ether;
10-phenoxydeca-2(Z),5(Z),8(Z)-trien-1-ol; and
10-phenoxydeca-2(Z),5(Z),8(Z)-trien-1-ol methanesulfonate.

A.

1-Iodo-10-phenoxydeca-2(Z),5(Z),8(Z)-triene

A solution of 2 g of 10-phenoxydeca-2(Z),5(Z),8(Z)-trien-1-ol methanesulfonate in 20 ml of acetone was treated with a solution of 2.766 g (0.0184 mol) of sodium iodide and 0.522 g (0.0061 mol) of sodium bicarbonate in 30 ml of acetone. The reaction mixture was stirred for 30 minutes at room temperature and then the solvent was removed under reduced pressure. The residue was diluted with water and extracted with methylene chloride, the organic extracts were dried and evaporated in vacuo. The crude material was purified by column chromatography on 40 g of silica gel using hexane-ethyl acetate (95:5) as eluant, thus obtaining the title compound, as an oil.

B.

13-Phenoxytrideca-5(Z),8(Z),11(Z)-trien-2-yn-1-ol methanesulfonate

To a cold ($-10°$ C.) solution of 1.42 g (10 mmol) of propargyl alcohol tetrahydropyranyl ether in 20 ml of anhydrous tetrahydrofuran, there was added dropwise, under stirring and under argon atmosphere, 2.49 ml (1.45 g, 10.8 mmol) of a 4.34N ethereal solution of ethylmagnesium bromide. The reaction mixture was stirred for 1 hour at $-10°$ C., allowed to attain room temperature and treated with 44.3 mg (0.44 mmol) of cuprous chloride. After 20 minutes at room temperature, the reaction mixture was heated to reflux and treated with 1.2 g (3.3 mmol) of 1-iodo-10-phenoxydeca-2(Z),5(Z),8(Z)-triene, refluxing for 3 additional hours. The reaction mixture was then poured into 50 ml of saturated ammonium chloride solution and extracted with ether. The organic extract was dried and evaporated in vacuo. Purification of the residue by column chromatography on 50 g of silica gel, using hexane-ethyl acetate (98:2) as eluant gave 13-phenoxytrideca-5(Z),8(Z),11(Z)-trien-2-yn-1-ol tetrahydropyranyl ether, as an oil.

The tetrahydropyranyloxy group was then hydrolyzed with Pyr/PTS in ethanol solution, and the alcohol esterified with methanesulfonyl chloride in the presence of triethylamine, in accordance with the method of Example 1, parts B and C, to produce the title compound, as an oil. This product was used in the next step without further purification.

C.

2-(13'-Phenoxytrideca-5'(Z),8(Z),11'(Z)-trien-2-ynyl-thio)benzoic acid methyl ester A mixture of 3 ml of absolute methanol and 34.5 mg (1.5 m atoms) of sodium was stirred for 15 minutes, cooled to 0° C. and to the sodium methoxide solution thus obtained there were added 126 mg (0.75 mmol) of methyl thiosalicylate followed by a solution of 175 mg of the mesylate obtained in part A, in 2 ml of absolute methanol. The reaction mixture was allowed to attain room temperature and stirred for 30 minutes, poured into 10 ml of water, acidified with saturated oxalic acid solution and extracted with methylene chloride. The combined extracts were dried over sodium sulfate and evaporated in vacuo. The residue was purified by thin layer chromatography, using hexane-ethyl acetate (80:20) as gradient (two developments), to yield the title compound, as an oil.

U.V.: $\lambda_{max}^{MeOH}$ 260, 316 nm ($\epsilon$ 28180, 3236).
I.R.: (CHCl$_3$) 1050, 1250, 1500, 1600, 1720, 3000 cm$^{-1}$.
N.M.R.: (CDCl$_3$) 2.78 (t, 2H); 2.87 (d, 4H); 3.68 (t, 2H); 3.94 (s, 3H COOCH$_3$); 4.6 (d, 2H); 5.32–5.78 (m, 6H); 6.87–7.5 (m, 9H).
M.S.: 450 (MNH$_4$)$^+$.

D.

2-(13'-Phenoxytrideca-5'(Z),8'(Z),11'(Z)-trien-2'-ynyl-thio)benzoic acid

A solution of 117.8 mg (0.27 mmol) of the foregoing methyl ester in 4 ml of a 0.5N methanolic sodium hydroxide solution was stirred at room temperature for 60 hours. The reaction mixture was then poured into 10 ml of water, acidified with saturated aqueous oxalic acid solution and extracted with methylene chloride. The extract was dried over sodium sulfate and evaporated in vacuo. The residue was purified by column chromatography on 10 g of silica gel, using methylene chloride methanol (98:2) as eluant, to yield the title compound, as an oil.

U.V.: $\lambda_{max}^{MeOH}$ 259, 314 nm. ($\epsilon$ 9333, 3548).
I.R.: (CHCl$_3$) 1240, 1500, 1600, 1700, 2940 cm$^{-1}$.
N.M.R.: (CDCl$_3$) 2.76 (t, 2H); 2.89 (t, 4H); 3.69 (t, 2H); 4.6 (d, 2H); 5.4–5.77 (m, 6H); 6.85–7.5 (m, 9H).
M.S.: 418 (M+).

EXAMPLE 11

2-(13'-Phenoxytrideca-2'(Z),5'(Z),8'(Z),11'(Z)-tetraenylthio)benzoic acid

A.

13-Phenoxytrideca-2(Z),5(Z),8(Z),11(Z)-tetraen-1-ol tetrahydropyranyl ether

A solution of 1.37 g (3.7 mmol) of 13-phenoxytrideca-5(Z),8(Z),11(Z)-trien-2-yn-1-ol tetrahydropyranyl ether in 50 ml of a (1:1) methanol-ethyl acetate mixture was hydrogenated at room temperature in the presence of 137 mg of pre-reduced Lindlar's catalyst and 0.35 ml of quinoline, until the calculated amount of hydrogen was consumed (119 ml, at atmospheric pressure of 585 mm Hg). The catalyst was separated by filtration through celite and the filtrate evaporated in vacuo. The residue was purified by silica gel column chromatography (20 g) eluting with hexane-ethyl acetate (98:2) to yield the title compound, as an oil.

B.

13-Phenoxytrideca-2(Z),5(Z),8(Z),11(Z)-tetraen-1-ol

To a solution of 1.22 g (3.3 mmol) of 13-phenoxytrideca-2(Z),5(Z),8(Z),11(Z)-tetraen-1-ol tetrahydropyranyl ether in 13 ml of 96% ethanol there were added 833 mg (3.3 mmol) of Pyr/PTS, and the reaction mixture was stirred for 2 hours at 55° C. It was then poured into water and extracted with methylene chloride. The extract was dried and evaporated. The crude material was purified by silica gel column chromatography (20 g) using hexane-ethyl acetate (90:10) as eluant, to yield the title compound, as an oil.

C.

13-Phenoxytrideca-2(Z),5(Z),8(Z),11(Z)-tetraen-1-ol methane sulfonate

To a solution of 150 mg (0.52 mmol) of 13-phenoxytrideca-2(Z),5(Z),8(Z),11(Z)-tetraen-1-ol in 6 ml of methylene chloride containing 0.12 ml (85 mg, 0.84 mmol) of triethylamine there was added 0.06 ml (90 mg, 0.78 mmol) of methanesulfonyl chloride, at 0° C. The resulting mixture was stirred for 15 minutes and poured into 30 ml of saturated aqueous sodium bicarbonate solution. After extraction with methylene chloride, the organic extract was dried and evaporated, to obtain the title mesylate, which was used in the next step without further purification.

D.

2-(13'-Phenoxytrideca-2'(Z),5'(Z),8'(Z),11'(Z)-tetraenylthio)benzoic acid methyl ester To 4 ml of absolute methanol, 36.4 mg (1.58 m atoms) of sodium was added. The mixture was stirred until complete dissolution, cooled to 0° C. and 133 mg (0.79 mmol) of methyl thiosalicylate were added, followed by a solution of 187.37 mg (517 mmol) of the crude mesylate previously obtained in 2 ml of absolute methanol. The mixture was warmed to room temperature and stirred for 30 minutes. It was then poured into 10 ml of water, acidified with saturated oxalic acid solution and extracted with methylene chloride; the organic extracts were dried and evaporated.

The residue was purified by thin layer chromatography, using hexane-ethyl acetate (90:10) as gradient, thus obtaining the title compound, as an oil.

U.V.: $\lambda_{max}^{MeOH}$ 262.5, 319 nm ($\epsilon$ 10,000, 3388).
I.R.: (CHCl$_3$) 1050, 1240, 1600, 1720, 3000 cm$^{-1}$.
N.M.R.: (CDCl$_3$) 3.8 (t, 6H); 3.56 (d, 2H); 3.9 (s, 3H, COOCH$_3$); 4.56 (d, 2H); 5.26–5.76 (m, 8H); 6.76–8.1 (m, 9H).
M.S.: 403 (M+—OCH$_3$).

E.

2-(13'-Phenoxytrideca-2'(Z),5'(Z),8'(Z),11'(Z)-tetraenylthio)benzoic acid

In accordance with the method of Example 10, part C, 153 mg (0.35 mmol) of the foregoing methyl ester were hydrolyzed with 5 ml of a 0.5N methanolic sodium hydroxide solution, to produce the title free acid, m.p. 44°–45° C. (Recrystallized from benzene-hexane).

EXAMPLE 12

3-(13'-Phenoxytrideca-2'(Z),5'(Z),8'(Z),11'(Z)-tetraenylthio)benzoic acid

Example 11, part D was repeated substituting methyl m-mercaptobenzoate for methyl thiosalicylate, obtaining 3-(13'-phenoxytrideca-2'(Z),5'(Z),8'(Z),11'(Z)-tetraenylthio)benzoic acid methyl ester as a oil.

U.V.: $\lambda_{max}^{MeOH}$ 262.5, 306 nm ($\epsilon$ 6026, 955).
I.R.: (CHCl$_3$) 1260, 1440, 1500, 1600, 1720, 2960 cm$^{-1}$.
N.M.R.: (CDCl$_3$) 2.78 (m, 6H); 3.58 (d, 2H); 3.9 (s, 3H COOCH$_3$); 4.58 (d, 2H); 5.2–5.8 (m, 8H); 6.76–8.1 (m, 9H).
M.S.: 452 (MNH$_4$)$^+$.

Upon hydrolysis of 144 mg (0.33 mmol) of the foregoing methyl ester with 0.5N methanolic sodium hydroxide solution, in accordance with the method of Example 10, part C, there were obtained the title compound, as an oil.

U.V.: $\lambda_{max}^{MeOH}$ 261, 308 nm ($\epsilon$ 5888, 977.2).
I.R.: (CHCl$_3$) 1240, 1490, 1600, 1690, 2920 cm$^{-1}$.
N.M.R.: (CDCl$_3$) 2.73 (m, 6H); 3.63 (d, 2H); 4.6 (d, 2H); 5.26–5.83 (m, 8H); 6.8–8.2 (m, 9H); 9.8 (s broad, 1H, COOH).
M.S.: 421 (MH$^+$).

EXAMPLE 13

2-(Octadeca-6'(Z),9'(Z),12'(Z)-trien-3'-ynyl)benzoic acid

A.

1-Iodotetradeca-2(Z),5(Z),8(Z)-triene

To a solution of 649 mg (4.3 mmol) of sodium iodide and 245 mg (2.8 mmol) of sodium bicarbonate in 20 ml of acetone there was added a solution of 400 mg of tetradeca-2(Z),5(Z),8(Z)-trien-1-ol methanesulfonate (obtained as described in Example 1, part C) in 5 ml of acetone. The reaction mixture was stirred at room temperature for 30 minutes and evaporated to dryness under reduced pressure. The residue was diluted with water and extracted with methylene chloride, and the organic extract dried and evaporated. The residue was purified by column chromatography on 10 g of silica gel, eluting with hexane, thus obtaining the title compound, as an oil.

B.

2-(Octadeca-6'(Z),9'(Z),12'(Z)-trien-3'-ynyl)benzoic acid methyl ester

A solution of 386 mg (2.05 mmol) of 2-(3-butyn-1-yl)benzoic cid methyl ester in 7 ml of anhydrous tetrahydrofuran was cooled to −70° C. and treated dropwise, under argon atmosphere with 1.57 ml (131.5 mg, 2.05 mmol) of a 1.31N solution of n-butyl lithium. The mixture was stirred for 45 minutes at −70° C. and then 195.7 mg (1.03 mmol) of cuprous iodide were added. After stirring for 20 minutes at the same temperature, 326.7 mg (1.03 mmol) of 1-iodotetradeca-2(Z),5(Z),8(Z)-triene dissolved in 3 ml of anhydrous tetrahydrofuran was added, stirring for 2 hours further at −20° C. The mixture was then poured into 15 ml of water, acidified with saturated oxalic acid solution and extracted with ethyl acetate. The combined extracts were dried and evaporated. The residue was purified by thin layer chromatography, using hexane-ethyl acetate (90:10) as gradient, to yield the title compound, as an oil.

U.V.: $\lambda_{max}^{MeOH}$ 231, 278.5 nm ($\epsilon$ 7762, 1259).
I.R.: (CHCl$_3$) 1085, 1130, 1265, 1435, 1600, 1720, 2940 cm$^{-1}$.
N.M.R.: (CDCl$_3$) 0.9 (t, 3H); 1.3 (m, 6H); 2.01 L (m, 2H); 2.18 (m, 2H); 2.85 (m, 6H); 3.16 (m, 2H); 3.9 (s, 3H); 5.2–5.66 (m, 6H); 7.13–8.06 (m, 4H).
M.S.: 378 (M$^+$).

C.

2-(Octadeca-6'(Z),9'(Z),12'(Z)-trien-3'-ynyl)benzoic acid

To a solution of 180 mg (0.47 mmol) of the methyl ester obtained in part B in 7 ml of dimethoxyethane and 2.3 ml of water, there were added 59.9 mg (1.42 mmol) of lithium hydroxide hydrate. The reaction mixture was stirred for 18 hours at room temperature and treated with 59.9 mg more of lithium hydroxide hydrate in 2 ml of water, stirring for 8 hours further at 40° C. The solvent was then evaporated under reduced pressure and the residue diluted with water, acidified with saturated oxalic acid solution and extracted with methylene chloride. The combined extracts were dried and evaporated. Purification of the residue by silica gel column chromatography (10 g), using methylene chloride-methanol (98:2) as eluant, yielded the title compound as an oil.

U.V.: $\lambda_{max}^{MeOH}$ 229, 277.5 nm ($\epsilon$ 7413, 1380).
I.R.: (CHCl$_3$) 970, 1370, 1455, 1600, 1695, 2920 cm$^{-1}$.
N.M.R.: (CDCl$_3$) 0.86 (t, 3H); 1.33 (m, 6H); 2.03 (m, 2H); 2.51 (m, 2H); 2.83 (m, 6H); 2.91 (t, 2H); 5.2–5.66 (m, 6H); 7.0–8.56 (m, 5H).
M.S.: 364 (M$^+$).

EXAMPLE 14

2-(Octadeca-3'(Z),6'(Z),9'(Z),12'(Z)-tetraenyl)benzoic acid

A.

2-(Octadeca-3'(Z),6'(Z),9'(Z),12'(Z)-tetraenyl)benzoic acid methyl ester

A solution of 319.6 mg (0.84 mmol) of 2-(octadeca-6'(Z),9'(Z),12'(Z)-trien-3'-ynyl)benzoic acid methyl ester in 15 ml of absolute methanol was hydrogenated at room temperature and atmospheric pressure in the presence of 31.9 mg of pre-reduced Lindlar's catalyst and 0.08 ml of quinoline, until the calculated amount of hydrogen was consumed (26 ml). The catalyst was separated by filtration through celite and the filtrate evaporated in vacuo. The residue was purified by thin layer chromatography, using hexane-isopropyl ether (98:2) as gradient (two developments), to yield the title compound, as an oil.

U.V.: $\lambda_{max}^{MeOH}$ 228, 279 nm ($\epsilon$ 8128, 1318).
I.R.: (CHCl$_3$) 975, 1285, 1070, 1440, 1600, 1720, 2940 cm$^{-1}$.
N.M.R.: (CDCl$_3$) 0.91 (t, 3H); 1.33 (m, 6H); 2.05 (m, 2H); 2.4 (m, 2H); 2.76 (m, 6H); 3.06 (t, 2H); 3.93 (s, 3H); 5.13–5.7 (m, 8H); 7.1–8.23 (m, 4H).
M.S.: 380 (M$^+$).

B.

2-(Octadeca-3'(Z),6'(Z),9'(Z),12'(Z)-tetraenyl)benzoic acid

To a solution of 110 mg (0.29 mmol) of the foregoing methyl ester in 1 ml of tetrahydrofuran there were added 8 ml of 80% aqueous methanol and 1.3 ml of a 0.5N solution of sodium hydroxide. The mixture was stirred at room temperature for 15 hours. The solvent was then evaporated and the residue diluted with 10 ml of water, acidified with saturated solution of oxalic acid and extracted with methylene chloride. The organic extracts were dried and evaporated. The residue was purified by column chromatography on 15 g of silica gel, using methylene chloride-methanol (98:2) as eluant, to yield the title compound, as an oil.

U.V.: $\lambda_{max}^{MeOH}$ 278 nm ($\epsilon$ 1349).
I.R.: (CHCl$_3$) 975, 1270, 1460, 1600, 1700, 2900 cm$^{-1}$.
N.M.R.: (CDCl$_3$) 0.86 (t, 3H); 1.3 (m, 6H); 1.96 (m, 2H); 2.36 (m, 2H); 2.71 (m, 6H); 3.11 (t, 2H); 5.1–5.63 (m, 8H); 7.16–8.2 (m, 4H); 8.6 (s broad, 1H, COOH).
M.S.: 366 (M+).

EXAMPLE 15

2-(Heptadeca-5'(Z),8'(Z),11'(Z)-trien-2'-ynyloxy)benzoic acid

A.

2-(Heptadeca-5'(Z),8'(Z),11'(Z)-trien-2'-ynyloxy)benzoic acid methyl ester

A suspension of 204 mg (4.26 mmol) of 50% sodium hydride in 20 ml of anhydrous dimethylformamide was treated with 617 mg (4.05 mmol) of methyl salicylate, stirring the mixture at room temperature for 15 minutes, and thereafter a solution of 620 mg (1.91 mmol) of heptadeca-5(Z),8(Z),11(Z)-trien-2-yn-1-ol methanesulfonate in 6 ml of dimethylformamide was added. The reaction mixture was stirred for 6 hours at room temperature, poured into water and extracted with a 1:1 mixture of benzene-ether. The organic extract was dried and evaporated under vacuo. The residue was purified by thin layer chromatography, using hexane-ethyl acetate (90:10) as gradient (3 developments) to yield the title compound, as an oil.

U.V.: $\lambda_{max}^{MeOH}$ 232, 287 nm ($\epsilon$ 10720, 3311).
I.R.: (CHCl$_3$) 1725, 1600 cm$^{-1}$.
N.M.R.: (CDCl$_3$) 0.90 (t, 3H); 1.33 (m, 6H); 2.04 (m, 2H); 2.78 (m, 2H); 2.89 (m, 4H); 3.9 (s, 3H, COOCH$_3$); 4.78 (m, 2H); 5.16–5.66 (m, 6H); 6.99–7.9 (m, 4H).
M.S.: 381 (MH+).

B.

2-(Heptadeca-5'(Z),8'(Z),11'(Z)-trien-2-ynyloxy)benzoic acid

The foregoing methyl ester (189 mg) was hydrolyzed with 0.5N sodium hydroxide in methanol (4 ml), 72 hours at room temperature. The crude product was purified by thin layer chromatography using methylene chloride-methanol (95:5) as gradient (2 developments) thus obtaining the subject acid, as an oil.

U.V.: $\lambda_{max}^{MeOH}$ 232, 289 nm ($\epsilon$ 7586, 2512).
I.R.: (CHCl$_3$) 3310, 1730, 1600, 1460 cm$^{-1}$.
N.N.R.: (CDCl$_3$) 0.95 (t, 3H); 1.30 (m, 6H); 2.03 (m, 2H); 2.78 (m, 2H); 2.98 (m, 4H); 4.94 (m, 2H); 5.40 (m, 6H); 7.03–8.34 (m, 4H).
M.S.: 367 (MH+).

EXAMPLE 16

2-(Heptadeca-2'(Z),5'(Z),8'(Z),11'(Z)-tetraenyloxy)benzoic acid

A.

2-Heptadeca-2'(Z),5'(Z),8'(Z),11'(Z)-tetraenyloxy)benzoic acid methyl ester

To a suspension of 129 mg (2.68 mmol) of 50% sodium hydride in 10 ml of anhydrous dimethylformamide there were added 389 mg (2.55 mmol) of methyl salicylate. The mixture was stirred at room temperature for 15 minutes and a solution of 385 mg (1.17 mmol) of heptadeca-2(Z),5(Z),8(Z),11(Z)-tetraen-1-ol methanesulfonate in 5 ml of dimethylformamide were added. The reaction mixture was stirred for 2 hours at room temperature, poured into water, acidified with saturated oxalic acid solution and extracted with methylene chloride. The organic extracts were dried and evaporated, and the residue purified in the chromatotron, using hexane-ethyl acetate (96:4) as gradient, to yield the title methyl ester, as an oil.

U.V.: $\lambda_{max}^{MeOH}$ 230, 292 nm ($\epsilon$ 7079, 2630).
I.R.: (CHCl$_3$) 1720, 1600 cm$^{-1}$.
N.M.R.: (CDCl$_3$) 0.90 (t, 3H); 1.33 (m, 6H); 2.06 (m, 2H); 2.86 (m, 6H); 3.86 (s, 3H, COOCH$_3$); 4.73 (m, 2H); 5.16–5.83 (m, 8H); 6.86–7.9 (m, 4H).
M.S.: 383 (MH+).

B.

2-(Heptadeca-2'(Z),5'(Z),8'(Z),11'(Z)-tetraenyloxy)benzoic acid 159 mg of the methyl ester obtained in part A were hydrolyzed with 6 ml of 0.5N methanolic sodium hydroxide solution, 16 hours at room temperature. The crude product was purified by column chromatography on 4 g of silica gel, eluting with hexane-ethyl acetate (97:3), to yield the subject free acid, as an oil.

U.V.: $\lambda_{max}^{MeOH}$ 230, 292 nm ($\epsilon$ 7079, 2692).
I.R.: (CHCl$_3$) 3300, 1735, 1600 cm$^{-1}$.
N.M.R.: (CDCl$_3$) 0.9 (t, 3H); 1.3 (m, 6H); 2.06 (m, 2H); 2.66–3.13 (m, 6H); 4.83 (m, 2H); 5.16–6.0 (m, 8H); 7.0–8.33 (m, 4H).
M.S.: 369 (MH+).

EXAMPLE 17

2-(13'-Phenoxytrideca-2'(Z),5'(Z),8'(Z),11'(Z)-tetraenyloxy)benzoic acid

Example 16 was repeated using in part A, 84.5 mg (0.69 mmol) of 13-phenoxytrideca-2(Z),5(Z),8(Z),11(Z)-tetraen-1-ol methanesulfonate as starting material, as well as the following amount of reagents: 84.5 mg (1.47 mmol) of 50% sodium hydride in 12 ml of anhydrous dimethylformamide and 214 mg (1.40 mmol) of methyl salicylate. There were obtained 2-(13'-phenoxytrideca-2'(Z),5'(Z),8'(Z),11'(Z)-tetraenyloxy)benzoic acid methyl ester, as an oil.

U.V.: $\lambda_{max}^{MeOH}$ 271.5, 278, 292 nm ($\epsilon$ 3020, 3388, 3090).
I.R.: (CHCl$_3$) 1085, 1240, 1495, 1600, 1720, 2970 cm$^{-1}$.
N.M.R.: (CDCl$_3$) 2.83 (t, 6H); 3.9 (s, 3H, COOCH$_3$); 4.63 (t, 4H); 5.23–5.93 (m, 8H); 6.76–7.9 (m, 9H).
M.S.: 436 (MNH$_4$+).

Upon hydrolysis of the foregoing methyl ester with 0.5N methanolic sodium hydroxide solution, followed by purification of the crude acid in the chromatotron, using hexane-ethyl acetate-acetic acid (80:20:1) as gradient, there was obtained the title compound as an oil, in 87% yield.

U.V.: $\lambda_{max}^{MeOH}$ 272, 278, 292 nm ($\epsilon$ 2818, 3162, 2764).
I.R.: (CHCl$_3$) 975, 1235, 1385, 1455, 1600, 1730, 3020, 3280 cm$^{-1}$.
N.M.R.: (CDCl$_3$) 2.9 (t, 6H); 4.6 (d, 2H); 4.83 (d, 2H); 5.23–5.93 (m, 8H); 6.76–8.3 (m, 9H); 10.5 (s broad, 1H, COOH).
M.S.: 422 (MNH$_4$+).

EXAMPLE 18

4-(Heptadeca-2'(Z),8'(Z),11'(Z)-trien-5-ynylthio)benzoic acid

A.

4-(Heptadeca-2'(Z),8'(Z),11'(Z)-trien-5-ynylthio)benzoic acid methyl ester

To 4 ml of absolute methanol, 36 mg 1.6 m atoms) of sodium were added. The mixture was stirred for 15 minutes until complete dissolution, cooled to 0° C. and treated with 133.1 mg (0.79 mmol) of methyl p-mercaptobenzoate, followed by a solution of 167.8 mg (0.51 mmol) of heptadeca-2(Z),8(Z),11(Z)-trien-5-yn-1-ol methanesulfonate in 2 ml of absolute methanol. The reaction mixture was allowed to attain room temperature and stirred for 30 minutes further. It was then poured into 15 ml of water, acidified with saturated solution of oxalic acid and extracted with methylene chloride; the combined extracts were dried and evaporated. The residue was purified by thin layer chromatography, using hexane-ethyl acetate (90:10) as gradient, to yield the title compound, as an oil.

U.V.: $\lambda_{max}^{MeOH}$ 227, 293 nm ($\epsilon$ 9120, 16220).
I.R.: (CHCl$_3$) 1100, 1280, 1430, 1600, 1720, 2920 cm$^{-1}$.
N.M.R.: (CDCl$_3$) 0.83 (t, 3H); 1.33 (m, 6H); 2.0 (m, 2H); 2.96 (m, 6H); 3.63 (t, 2H); 3.9 (s, 3H, COOCH$_3$); 5.2–6 (m, 6H); 7.3 (d, 2H); 7.95 (d, 2H).
M.S.: 396 (M+).

B.

Upon hydrolysis of 131 mg of the foregoing methyl ester with 0.5N sodium hydroxide in methanol, in accordance with the method of Example 10, there were obtained 4-(heptadeca-2'(Z),8'(Z),11'(Z)-trien-5-ynylthio)benzoic acid, as an oil.

U.V.: $\lambda_{max}^{MeOH}$ 288 nm ($\epsilon$ 12590).
I.R.: (CHCl$_3$) 950, 1230, 1410, 1590, 1700, 2900 cm$^{-1}$.
N.M.R.: (CDCl$_3$) 0.86 (t, 3H); 1.38 (m, 6H); 2.03 (m, 2H); 2.83 (m, 6H); 3.61 (d, 2H); 5.2–5.86 (m, 6H); 7.3 (d, 2H); 8.0 (d, 2H); 8.9 (s broad, 1H, COOH).
M.S.: 400 (MNH$_4$+).

EXAMPLE 19

3-(Heptadeca-2'(Z),8'(Z),11'(Z)-trien-5-ynylthio)benzoic acid

This compound was prepared in accordance with the method of Example 19, substituting in part A, methyl m-mercaptobenzoate for the corresponding p-isomer. The following reagent quantities were used:

Sodium 42 mg (1.82 m atoms) in 5 ml of absolute methanol
Methyl m-mercaptobenzoate 153.6 mg (0.914 mmol)
Heptadeca-2(Z),8(Z),11(Z)-trien-5-yn-1-ol methanesulfonate 193.6 mg (0.59 mmol) in 2 ml of absolute methanol.

There were obtained 3-(heptadeca-2'(Z),8'(Z),11'(Z)-trien-5-ynylthio)benzoic acid methyl ester, as an oil.

U.V.: $\lambda_{max}^{MeOH}$ 208, 260, 308 nm ($\epsilon$ 19950, 5888, 955).
I.R.: (CHCl$_3$) 950, 1260, 1440, 1580, 1730, 2920 cm$^{-1}$.
N.M.R.: (CDCl$_3$) 0.9 (t, 3H); 1.3 (m, 6H); 2.03 (M, 2H); 2.85 (m, 6H); 3.56 (d, 2H); 3.9 (s, 3H, COOCH$_3$); 5.16–6.0 (m, 6H); 7.2–8.2 (m, 4H).
M.S.: 414 (MNH$_4$+).

The methyl ester group was hydrolyzed with 0.5N methanolic sodium hydroxide solution. From 137 mg of the esterified compound there were obtained 62.4 mg (47%) of the title free acid, as an oil.

U.V.: $\lambda_{max}^{MeOH}$ 208, 259, 306 nm ($\epsilon$ 21880, 6457, 1047).
I.R.: (CHCl$_3$) 950, 1270, 1420, 1580, 1700, 2920 cm$^{-1}$.
N.M.R.: (CDCl$_3$) 0.86 (t, 3H); 2.36 (m, 6H); 2.01 (m, 2H); 2.8 (m, 6H); 3.58 (d, 2H); 5.16–6.0 (m, 6H); 7.23–8.16 (m, 4H); 9.5 (s broad, 1H, COOH).
M.S.: 400 (MNH$_4$+).

EXAMPLE 20

2-(Heptadeca-2'(Z),8'(Z),11'(Z)-trien-5-ynylthio)benzoic acid

Example 19 was repeated using as reagent in part A, methyl o-mercaptobenzoate in place of the p-isomer, thus obtaining 2-(heptadeca-2'(Z),8'(Z),11'(Z)-trien-5-ynylthio)benzoic acid methyl ester as an oil, which has the following constants:

U.V.: $\lambda_{max}^{MeOH}$ 233, 264, 324 nm ($\epsilon$ 11480, 7079, 2512).
I.R.: (CHCl$_3$) 950, 1050, 1250, 1430, 1600, 1720, 2920 cm$^{-1}$.
N.M.R.: (CDCl$_3$) 0.91 (t, 3H); 1.3 (m, 6H); 2.05 (m, 2H); 2.83 (m, 6H); 3.58 (d, 2H); 3.9 (s, 3H, COOCH$_3$); 5.16–5.93 (m, 6H); 7.03–8.1 (m, 4H).
M.S.: 396 (M+).

The foregoing methyl ester was hydrolyzed with 5 ml of 0.5N sodium hydroxide in methanol, 20 hours at room temperature. From 150 mg of the esterified compound there were obtained the title free acid, as an oil.

U.V.: $\lambda_{max}^{MeOH}$ 263, 321 nm ($\epsilon$ 5248, 1950).
I.R.: (CHCl$_3$) 950, 1250, 1470, 1700, 2930 cm$^{-1}$.
N.M.R.: (CDCl$_3$) 0.88 (t, 3H); 1.36 (m, 6H); 2.0 (m, 2H); 2.93 (m, 6H); 3.58 (d, 2H); 5.2–5.93 (m, 6H); 7.06–8.23 (m, 4H); 9.96 (s broad, 1H, COOH).
M.S.: 400 (MNH$_4$+).

EXAMPLE 21

2-(Heptadeca-5'(Z),11'(Z)-dien-2',8'-diynylthio)benzoic acid

A.

Tetradeca-2(Z),8(Z)-dien-5-yn-1-ol methanesulfonate

To a cooled (0° C.) solution of 1.65 g (7.99 mmol) of tetradeca-2(Z),8(Z)-dien-5-yn-1-ol (U.S. Pat. No. 4,497,827) in 30 ml of dry methylene chloride, 1.8 ml (12.7 mmol) of triethylamine and 0.92 ml (11.9 mmol) of methanesulfonyl chloride were added. The mixture was stirred for 90 minutes at 0° C., diluted with 50 ml of methylene chloride, washed with brine, dried and evaporated under vacuum, to provide the title mesylate.

B.

1-iodotetradeca-2(Z),8(Z)-dien-5-yne

A solution of the crude mesylate (2.18 g, 7.66 mmol) in 20 ml of acetone was added to a mixture of 1.2 g (8 mmol) of sodium iodide, 10 ml of acetone and 0.5 g (5.9 mmol) of sodium bicarbonate. The mixture was stirred at room temperature for 30 minutes, the solvent was removed under vacuum and the residue partitioned between ether and water. The organic layer was washed with brine, dried and evaporated. Purification by column chromatography on 50 g of silica gel, using hexane as eluant, provided the title compound, as an oil.

C.

Heptadeca-5(Z),11(Z)-dien-2,8-diyn-1-ol tetrahydropyranyl ether

To a stirred solution of 1.6 g (11.12 mmol) of propargyl alcohol tetrahydropyranyl ether in 20 ml of dry tetrahydrofuran there were added dropwise, under argon atmosphere, 3.05 ml (11.12 mmol) of a 3.5N solution of ethylmagnesium bromide in ether, maintaining the temperature at 5° C. The mixture was refluxed for 1 hour, cooled to room temperature and 42 mg of cuprous chloride were added. The reaction mixture was stirred for 15 minutes further and then a solution of 1.85 g (5.84 mmol) of 1-iodotetradeca-2(Z),8(Z)-dien-5-yne in 25 ml of dry tetrahydrofuran was added dropwise, during 15 minutes. The mixture was refluxed for 4 hours, cooled to room temperature, diluted with ether, washed with saturated ammonium chloride solution and water, dried and evaporated under vacuo. After column chromatography on 200 g of silica gel, there was obtained an 80:20 mixture of the title compound and recovered propargyl alcohol tetrahydropyranyl ether. This mixture (2.1 g) was used in the next step without further purification.

D.

Heptadeca-5(Z),11(Z)-dien-2,8-diyn-1-ol methanesulfonate

The foregoing mixture was submitted to hydrolysis of the tetrahydropyranyloxy function with Pyr/PTS in ethanol and esterification of the hydroxy group with methanesulfonyl chloride, in accordance with the method of Example 2, parts A and B,-to produce the title compound, as an oil.

E.

2-(Heptadeca-5'(Z),11'(Z)-dien-2',8'-diynylthio)benzoic acid methyl ester

A solution of 185 mg (0.57 mmol) of the foregoing mesylate were treated with 105 mg (0.62 mmol) of methyl thiosalicylate in the presence of sodium methoxide (obtained from 32 mg (1.5 m atoms of sodium and 3 ml of absolute methanol) in accordance with the method of Example 2, part C, to produce the title compound, as an oil.

U.V.: $\lambda_{max}^{MeOH}$ 229, 262, 321 nm ($\epsilon$ 15140, 4898, 2754).

I.R.: (CHCl$_3$) 1715, 1590 cm$^{-1}$.

N.M.R.: (CDCl$_3$) 0.86 (t, 3H); 1.3 (m, 6H); 2.0 (m, 2H); 2.9 (m, 6H); 3.66 (s, 2H); 3.9 (s, 3H, COOC$\underline{H}_3$); 5.26–5.83 (m, 4H); 7.06–8.13 (m, 4H).

M.S.: 394 (M+).

Similarly, substituting methyl p-thiolbenzate for methyl thiosalicylate 3-(Heptadeca-5'(Z),11'(Z)-dien-2',8'-diynylthio)benzoic acid methyl ester was made.

F.

2-(Heptadeca-5'(Z),11'(Z)-dien-2',8'-diynylthio)benzoic acid

A solution of 150 mg of the above-mentioned methyl ester in 4 ml of a 0.5N methanolic sodium hydroxide solution was stirred at room temperature for 20 hours. Upon the usual work up followed by purification by column chromatography on 5 g of silica gel, using methylene chloride as eluant, there were obtained the title free acid, as a solid with a low melting point.

U.V.: $\lambda_{max}^{MeOH}$ 228, 262, 320 nm ($\epsilon$ 15850, 7586, 3631).

I.R.: (CHCl$_3$) 3550, 1690, 1590 cm$^{-1}$.

N.M.R.: (CDCl$_3$) 0.86 (t, 3H); 1.26 (m, 6H); 2.0 (m, 2H); 2.9 (s, 6H); 3.66 (s, 2H); 5.26–5.8 (m, 4H); 7.06–8.26 (m, 4H).

M.S.: 381 (MH+).

EXAMPLE 22

2-(Heptadeca-2'(Z),5'(Z),8'(Z)-trien-11'-ynylthio)benzoic acid

A.

Deca-2,5,8-triyne-1,10-diol-1-monotetrahydropyranyl ether

To a solution of 1 g (10.6 mmol) hexa-2,5-diyn-1-ol [Recueil 82, 1015 (1963)] in 10 ml of dry tetrahydrofuran, there were added dropwise, under argon atmosphere, 2.95 ml (10 mmol) of 3.5N ethylmagnesium bromide, maintaining the temperature at 0° C. The mixture was stirred for 1 hour at 15° C. and 0.07 g of cuprous chloride were added, stirring for 20 minutes further. Then, a solution of 3.22 g (13.8 mmol) of 1-bromobut-2-yn-4-ol tetrahydropyranyl ether in 20 ml of dry tetrahydrofuran was added. The mixture was stirred for 2 hours at room temperature, 40 ml of saturated ammonium chloride solution was added and the product extracted with ether. The organic extracts were washed with water, dried and evaporated in vacuo. The residue was purified by column chromatography on 120 g of silica gel, eluting with hexane-ethyl acetate (80:20) thus yielding the title compound, as an oil.

B.

Deca-2(Z),5(Z),8(Z)-triene-1,10-diol 10-monotetrahydro-pyranyl ether

A solution of 520 mg (2.1 mmol) of the preceding compound in 12 ml of methanol was hydrogenated at room temperature and atmospheric pressure (585 mm Hg) in the presence of 60 mg of pre-reduced Lindlar's catalyst and 0.25 ml of quinoline, until 3 molar equivalents of hydrogen had been consumed. The catalyst was filtered through celite and the filtrate evaporated in vacuo. Purification of the residue by silica gel column chromatography (30 g) using hexane-ethyl acetate (85:15) as eluant gave the title compound, as an oil.

C.

1-Methanesulfonyloxy-10-tetrahydropyranyloxy-deca-2(Z),5(Z),8(Z)-triene

A solution of 780 mg (3.1 mmol) of deca-2(Z),5(Z),8(Z)-triene-1,10-diol-10-tetrahydropyranyl ether in 10 ml of dry methylene chloride, cooled to 0° C. was treated with 0.56 ml (4.03 mmol) of triethylamine and 0.28 ml (3.72 mmol) of methanesulfonyl chloride. The reaction was complete in 45 minutes, as demonstrated by t.l.c. analysis. It was then diluted with 10 ml of methylene chloride, washed with brine, dried and evaporated under vacuo, thus obtaining the crude title mesylate, which was used immediately without further purification.

D.

1-Iododeca-2(Z),5(Z),8(Z)-trien-10-ol tetrahydropyranyl ether

To a suspension of 424 mg (2.8 mmol) of sodium iodide in 5 ml of acetone was added a solution of 890 mg (2.7 mmol) of the foregoing crude mesylate in 4 ml of acetone. The reaction mixture was stirred at room temperature for 30 minutes; the solvent was removed under vacuum and the residue was partitioned between methylene chloride (15 ml) and water (15 ml), the organic layer was dried and evaporated. Purification of the residue by silica gel column chromatography afforded the title iodo derivative.

E.

Heptadeca-2(Z),5(Z),8(Z)-trien-11-yn-1-ol tetrahydropyranyl ether

A cooled (0° C.) solution of 490 mg (5.09 mmol) of 1-heptyne in 10 ml of anhydrous tetrahydrofuran was treated dropwise, under argon atmosphere with 1.71 ml (5.1 mmol) of a 4N solution of ethylmagnesium bromide in ether. The resulting mixture was stirred at 0° C. for 1 hour and then 35 mg of cuprous chloride were added. After stirring for 15 minutes more, a solution of 620 mg (1.7 mmol) of the iodo compound obtained in part D, in 10 ml of anhydrous tetrahydrofuran was added dropwise. The reaction was heated to reflux for 90 minutes, cooled, and diluted with 8 ml of saturated ammonium chloride solution. The product was extracted with ether. The combined extracts were washed with brine, dried and evaporated in vacuo. The residue was purified by thin layer chromatography using hexane-ethyl acetate (95:5) as gradient, to produce the title compound, as an oil.

F.

Heptadeca-2(Z),5(Z),8(Z)-trien-11-yn-1-ol methanesulfonate

A solution of 235 mg of the foregoing tetrahydropyranyl ether in 4 ml of 96% ethanol was treated with 30 mg (0.12 mmol) of Pyr/PTS. The reaction mixture was heated for 4½ hours at 55° C., the solvent removed under vacuo and the residue taken up in methylene chloride, washed with brine, dried and evaporated. Purification by column chromatography on 10 g of silica gel, using hexane-ethyl acetate (95:5) as eluant, afforded heptadeca-2(Z),5(Z),8(Z)-trien-11-yn-1-ol, an oil which was esterified with methanesulfonyl chloride in the presence of triethylamine, according to the method of part C of this Example, thus obtaining the title compound.

G.

2-(Heptadeca-2'(Z),5'(Z),8'(Z)-trien-11'-ynylthio)benzoic acid

By following the method of Example 2, part C, 140 mg (0.49 mmol) of the crude mesylate obtained above in 5 ml of dry methanol were condensed with 100 mg (0.6 mmol) of methyl thiosalicylate in the presence of sodium methoxide (prepared from 25 mg of sodium and 2 ml of methanol), to produce 150 mg of 2-(heptadeca-2'(Z),5'(Z),8'(Z)-trien-11'-ynylthio)benzoic acid methyl ester, as an oil.

The methyl ester group was then hydrolyzed with 0.5N methanolic sodium hydroxide, 60 hours at room temperature, thus obtaining the title free acid, as an oil.

In a similar manner, substituting methyl-m-mercaptobenzoate and methyl p-mercaptobenzoate for methyl thiosalicylate, there can be obtained:

3-(heptadeca-2'(Z),5'(Z),8'(Z)-trien-11'-ynylthio)benzoic acid, and 4-(heptadeca-2'(Z),5'(Z),8'(Z)-trien-11'-ynylthio)benzoic acid, respectively, via the corresponding methyl esters.

EXAMPLE 23

2-(Heptadeca-2'(Z),5'(Z),8'(Z)-trien-11-ynyloxy)benzoic acid

In accordance with the method of Example 15, 150 mg of heptadeca-2(Z),5(Z),8(Z)-trien-11-yn-1-ol methanesulfonate in 3 ml of dimethylformamide were treated with 150 mg of methyl salicylate in the presence of sodium hydride in dimethylformamide, can produce the title compound, as an oil.

EXAMPLE 24

Examples 1 and 2 were repeated using undeca-2,5,8-triyn-1-ol tetrahydropyranyl ether [D. Van der Steen et al, Recueil, 82, 1015 (1963)] and trideca-2,5,8-triyn-1-ol tetrahydropyranyl ether [(R. K. Beerthuis et al, Recueil, 87, 461 (1968)] as starting materials, can produce as final products:

tetradeca-5'(Z),8'(Z),11'(Z)-trien-2'-ynylthio)benzoic acid, and hexadeca-5'(Z),8'(Z),11'(Z)-trien-2'-ynylthio)benzoic acid.

EXAMPLE 25

2-[(13'-substituted phenoxy)-trideca-5'(Z),8'(Z),11'(Z)-trien-2'-ynylthio]-benzoic acid In accordance with the method of Example 10, starting from 10-(p-methylphenoxy)deca-2,5,8-triyn-1-ol tetrahydropyranyl ether there can be obtained:

10-(p-methylphenoxy)deca-2(Z),5(Z),8(Z)-trien-1-ol tetrahydropyranyl ether;

10-(p-methylphenoxy)deca-2(Z),5(Z),8(Z)-trien-1-ol;

10-(p-methylphenoxy)deca-2(Z),5(Z),8(Z)-trien-1-ol methanesulfonate;

1-iodo-10-(p-methylphenoxy)deca-2(Z),5(Z),8(Z)-triene;

13-p-methylphenoxytrideca-5(Z),8(Z),11(Z)-trien-2-yn-1-ol tetrahydropyranyl ether;

13-p-methylphenoxytrideca-5(Z),8(Z),11(Z),-trien-2-yn-1-ol;

13-(p-methylphenoxy)trideca-5(Z),8(Z),11(Z)-trien-2-yn-1-ol methanesulfonate;

2-[(13'-p-methylphenoxy)trideca-5'(Z),8'(Z),11'(Z)-trien-2'-ynylthio]benzoic acid methyl ester; and 2-[(13'-p-methylphenoxy)trideca-5'(Z),8'(Z),11'(Z)-trien-2'-ynylthio]benzoic acid.

Likewise, from the corresponding 1-tetrahydropyranyloxy-10-substituted phenoxy (or thiophenyl)-deca-2,5,8-tryines, there were obtained as final products:

2-[(13'-m-methoxyphenoxy)trideca-5'(Z),8'(Z),11'(Z)-trien-2'-ynylthio]benzoic acid;

2[(13'-m-fluorophenoxy)trideca-5'(Z),8'(Z),11'(Z)-trien-2'-ynylthio]benzoic acid;

2-[(13'-o-bromophenoxy)trideca-5'(Z),8'(Z),11'(Z)-trien-2'-ynylthio]benzoic acid;
2-[(13'-p-butylphenoxy)trideca-5'(Z),8'(Z),11'(Z)-trien-2'-ynylthio]benzoic acid;
2-[(13'-m-trifluoromethylphenoxy)trideca-5'(Z),8'(Z),11'(Z)-trien-2'-ynylthio]benzoic acid;
2-[(13'-p-cyanophenoxy)trideca-5'(Z),8'(Z),11'(Z)-trien-2'-ynylthio]benzoic acid;
2-[(13'-phenylthio)trideca-5'(Z),8'(Z),11'(Z)-trien-2'-ynylthio]benzoic acid; and
2-[(13'-p-methylphenylthio)trideca-5'(Z),8'(Z),11'(Z)-2'-ynylthio]benzoic acid.

EXAMPLE 26

By the method of Example 13, part B, the methyl esters of 2-(4-n-pentynyl)benzoic acid and 2(5n-hexynyl)benzoic acid can be coupled with 1-iodotetradeca-2(Z),5(Z),8(Z)-triene, to produce:
2-(nonadeca-7'(Z),10'(Z),13'(Z)-trien-4'-ynyl)benzoic acid methyl ester, and
2-(eicosa-8'(Z),11'(Z),14'(Z)-trien-5'-ynyl)benzoic acid methyl ester, respectively.

Upon hydrolysis of the methyl ester group with lithium hydroxide hydrate, in accordance with the method of Example 13, part C, the corresponding free acids were obtained.

EXAMPLE 27

Example 11 was repeated using 13-p-methylphenoxy-trideca-5(Z),8(Z),11(Z)-trien-2-yn-1-ol tetrahydropyranyl ether as starting material, to produce 2-[(13'-p-methylphenoxy)trideca-2'(Z),5'(Z),8'(Z),11'(Z)-tetraenylthio]benzoic acid as final product. Likewise but substituting in part D m-mercaptobenzoate and p-mercaptobenzoate for methyl thiosalicylate, there can be obtained:
3-[(13'-p-methylphenoxy)trideca-2'(Z),5'(Z),8'(Z),11'(Z)-tetraenylthio]benzoic acid, and
4-[(13'-p-methylphenoxy)trideca-2'(Z),5'(Z),8'(Z),11'(Z)-tetraenylthio]benzoic acid, respectively, via the corresponding methyl esters.

EXAMPLE 28

By following the method of Example 16 using as starting materials:
13-(p-methylphenoxy)trideca-5(Z),8(Z),11(Z)-trien-2-yn-1-ol methanesulfonate;
13-(m-trifluoromethylphenoxy)trideca-5(Z),8(Z),11(Z)-trien-2-yn-1-ol methanesulfonate;
heptadeca-5(Z),11(Z)-dien-2,8-diyn-1-ol methanesulfonate;
heptadeca-2(Z),8(Z),11(Z)-trien-5-yn-1-ol methanesulfonate;
heptadeca-2(Z),5(Z),8(Z)-trien-11-yn-1-ol methanesulfonate; and
octadeca-5(Z),8(Z),11(Z)-trien-2-yn-1-ol methanesulfonate there were obtained as final products:
2-[(13'-p-methylphenoxy)trideca-5'(Z),8'(Z),11'(Z)-trien-2'-ynyloxy]benzoic acid;
2-[(13'-m-trifluoromethylphenoxy)trideca-5'(Z),8'(Z),11'(Z)-trien-2'-ynyloxy]benzoic acid;
2-(heptadeca-5'(Z),11'(Z)-diene-2',8'-diynyloxy)benzoic acid;
2-(heptadeca-2'(Z),8'(Z),11'(Z)-trien-5'-ynyloxy)benzoic acid;
2-(heptadeca-2'(Z),5'(Z),8'(Z)-trien-11'-ynyloxy)benzoic acid; and
2-(octadeca-5'(Z),8'(Z),11'(Z)-trien-2'-ynyloxy)benzoic acid, respectively, via the corresponding methyl esters.

EXAMPLE 29

Preparation of alkyl esters

To a solution of 20 mg of 2-(heptadeca-5'(Z),8'(Z),11'(Z)-trien-2'-ynylthio)benzoic acid in 5 ml of ether there was added dropwise an ethereal solution of diazoethane until the color of the reagent persisted in the mixture. After 15 minutes at room temperature the solvent and excess reagent were eliminated under vacuum, and the residue purified by thin layer chromatography, to produce 2-(heptadeca-5'(Z),8'(Z),11'(Z)-trien-2'-ynylthio)benzoic acid ethyl ester.

In a similar manner, the free acids obtained in the previous Examples can be converted into the corresponding ethyl esters. Representative compounds thus obtained are:
4-(heptadeca-5'(Z),8'(Z),11'(Z)-trien-2'-ynylthio)-benzoic acid ethyl ester;
2-(octadeca-5'(Z),8'(Z),11'(Z)-trien-2'-ynylthio)-benzoic acid ethyl ester;
2-(octadeca-6'(Z),9'(Z),12'(Z)-trien-3'-ynylthio)-benzoic acid ethyl ester;
2-(13'-phenoxytrideca-5'(Z),8'(Z),11'(Z)-trien-2'-ynylthio)benzoic acid ethyl ester;
3-(13'-phenoxytrideca-2'(Z),5'(Z),8'(Z),11'(Z)-tetraenylthio)benzoic acid ethyl ester;
4-(heptadeca-2'(Z),8'(Z),11'(Z)-trien-5-ynylthio)-benzoic acid ethyl ester; and
2-(heptadeca-5'(Z),11'(Z)-dien-2',8'-diynylthio)-benzoic acid ethyl ester.

Likewise, substituting diazopropane or other lower diazoalkanes for diazoethane in the above-described procedure, the corresponding alkyl esters were prepared.

EXAMPLE 30

To a solution of 50 mg of 2-(heptadeca-5'(Z),11'(Z)-dien-2',8'-diynylthio)benzoic acid in 5 ml of methanol there was added 1.0 molar equivalent of a 0.1N solution of sodium bicarbonate, and the mixture was stirred at room temperature for 1 hour. The solvent was then eliminated under vacuo, to yield the sodium salt of 2-(heptadeca-5'(Z),11'(Z)-dien-2',8'-diynylthio)benzoic acid.

By applying one molar equivalent of potassium bicarbonate (in the form of a 0.1N solution) in place of sodium bicarbonate in the above procedure the potassium salt of 2-(heptadeca-5'(Z),11'(Z)-dien-2',8'-diynylthio)benzoic acid was prepared. Similarly, the sodium and potassium salts of the benzoic acid derivatives obtained in the previous Examples can be prepared.

EXAMPLE 31

To a solution of 50 mg of 4-(heptadeca-5'(Z),8'(Z),11'(Z)-trien-2'-ynylthio)benzoic acid in 3 ml of methanol was added a mixture of 2 ml of concentrated ammonium hydroxide solution and 2 ml of methanol. The resulting mixture was stirred for 2 hours at room temperature and then evaporated to dryness in vacuo, to yield the ammonium salt of 4-(heptadeca-5'(Z),8'(Z),11'(Z)-trien-2'-ynylthio)benzoic acid, which was purified by thin layer chromatography.

By employing 1.1 molar equivalents of trimethylamine, diethylamine and dipropylamine in place of ammonium hydroxide in the above procedure, the corresponding salts of 4-(heptadeca-5'(Z),8'(Z),11'(Z)-trien-2'-ynylthio)benzoic acid were obtained. In a similar manner, the ammonium, trimethylamine, diethylamine and dipropylamine salts of the other trien-ynyl, dien-ynyl, and tetraenylthio (or oxy) benzoic acids of the previous Example can be prepared.

EXAMPLE 32

A solution of 50 mg of 2-(13'-phenoxytrideca-2'(Z),5'(Z),8'(Z),11'(Z)-tetraenylthio)benzoic acid in 10 ml of 90% aqueous methanol was treated with 1.0 molar equivalent of procaine an the resultant reaction mixture was stirred at room temperature for 16 hours. It was then evaporated to dryness under reduced pressure, to give the procaine salt of 2-(13'-phenoxytrideca-2'(Z),5'(Z),8'(Z),11'(Z)-tetraenylthio)benzoic acid. Similarly, the lysine, caffeine and tromethamine salts thereof were prepared, as well as the corresponding salts of 3-(heptadeca-5'(Z),8'(Z),11'(Z)-trien-2'-ynylthio)benzoic acid;
2-(octadeca-5'(Z),8'(Z),11'(Z)-trien-2'-ynyl)benzoic acid;
2-(octadeca-3'(Z),6'(Z),9'(Z),12'(Z)-tetraenyl)benzoic acid, and
2-(heptadeca-5'(Z),11'(Z)-dien-2',8'-diynylthio)benzoic acid.

EXAMPLE 33

The following example illustrates the preparation of representative pharmaceutical formulations containing an active compound of formula I, e.g., 2-(heptadeca-5'(Z),8'(Z),11'(Z)-trien-2'-ynylthio)benzoic acid.

| I.V. Formulation | |
| --- | --- |
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

Other compounds of Formula A and the pharmaceutically acceptable salts thereof may be substituted therein.

EXAMPLE 34

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 35

| Ingredients | Quantity per capsule, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 36

| Ingredients | Quantity per tablet, mgs. |
| --- | --- |
| Active ingredient | 1 |
| cornstarch | 50 |
| lactose | 145 |
| magnesium stearate | 5 |

The above ingredients are mixed intimately and pressed into single scored tablets.

EXAMPLE 37

Topical Formulation

This formulation is a variation of Beeler's Base (See Remington's Pharmaceutical Sciences, 15th Ed., p. 1534)

| Active ingredient | 1 g |
| --- | --- |
| Cetyl Alcohol | 15 g |
| White Wax | 1 g |
| Propylene Glycol | 10 g |
| Sodium Lauryl Sulfate | 2 g |
| Water | 72 g |

The cetyl alcohol, white wax and active ingredient are heated together at about 65° C. in propylene glycol. The sodium lauryl sulfate and water are mixed together. The two solutions are then mixed together, and stirred well. The well mixed solution is removed from the heat and mixed to the point of congealing.

The above ingredients are mixed and introduced into a hard-shell gelatin capsule.

EXAMPLE 38

| Ingredients | Quantity per tablet, mgs. |
| --- | --- |
| Active ingredient | 150 |
| lactose | 92 |

The above ingredients are mixed and introduced into a hard-shell gelatin tablet.

EXAMPLE 39

An injectable preparation buffered to a pH of 7 is prepared having the following composition:

| Ingredients | |
| --- | --- |
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE 40

An oral suspension is prepared having the following composition:

| Ingredients | |
| --- | --- |
| Active ingredient | 0.1 g |
| fumaric acid | 0.5 g |
| sodium chloride | 2.0 g |

| Ingredients | |
|---|---|
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 41

Conversion of 2-(heptadeca-5'(Z),8'(Z),11'(Z)-trien-2'-ynylthio)benzoic acid

Sodium methoxide (82 mg) is added to a solution of 2-(heptadeca-5'(Z),8'(Z),11'(Z)-trien-2'-ynylthio)benzoic acid (500 mg) in methanol (5 ml). The solution is then evaporated to dryness to afford 2-(heptadeca-5'(Z),8'(Z),11'(Z)-trien-2'-ynylthio)benzoic acid sodium salt.

In a similar manner, all compounds of formula (A), may be converted to salts such as potassium, lithium, ammonium, calcium, magnesium, ferrous, zinc, copper, manganous, aluminum, ferric, manganic salts and the like.

EXAMPLE 42

Conversion of 2-(heptadeca-5'(Z),8'(Z),11'(Z)-trien-2'-ynylthio)benzoic Sodium Salt into 2-(heptadeca-5'(Z),8'(Z),11'(Z)-trien-2'-ynylthio)benzoic acid A two-fold stoichiometric excess of N hydrochloric acid is added to a solution of 2-(heptadeca-5'(Z),8'(Z),11'(Z)-trien-2'-ynylthio)benzoic acid sodium salt in water. The solution is then extracted with ether, and the extract is dried and evaporated to afford 2-(heptadeca-5'(Z),8'(Z),11'(Z)-trien-2'-ynylthio)benzoic acid.

EXAMPLE 43

Assay for Inhibition of Lipoxygenase Activity by Human Polymorphonuclear Leukocytes (PMNS)

Experimental Procedures

1. Preparation of the cells:

The PNMs are prepared from 200–300 ml of heparinized blood of healthy donors not receiving any medication for at least 7 days using Ficol-Hypaque gradients. In general, PMNs are greater than 90% pure and their viability is assessed by dye-exclusion to be better than 95%. The cells are suspended in phosphate buffered saline containing 1.0 mM $CaCl_2$ (pH 7.4) and 0.1% ovalbumin, and used within 30 minutes.

2. Lipoxygenase Assay:

Incubations are carried out at 37° C. for 5 minutes in a total volume of 0.2 ml arachidonic acid 1-$C^{14}$ ($1\times10^{-4}$M unless otherwise indicated, and approximately 300,000 cpm) is added to a suspension of cells (ca $5\times10^6$) to initiate the reaction. Prior to the addition of above substrate, the test substances are added to the cells at appropriate concentrations and pre-incubated at 37° C. for 5 minutes. In general, stock solutions of test substances are prepared in ethanol (or other appropriate solvents) and diluted with either incubation-buffer or water. The final concentration of ethanol in the incubation did not exceed 1%. Boiled enzyme blanks and controls containing no test compound are always included. The incubations are terminated by the addition of 0.6 ml of methanol, vortexed and kept on ice for 30 minutes.

1.6 ml of deionized water is added, vortexed, centrifuged, the supernatants decanted and kept in the freezer overnight. Separation of arachidonic acid and lipoxygenase products are carried out using "Baker" disposable $C-{18}$ extraction columns (1 ml capacity). The columns are prewashed with MeOH (2.0 ml) followed by deionized water (2 ml). After most of the solvent is removed, 2.0 ml of the supernatant is applied to the extraction columns and the solvent is allowed to flow through. The columns are then washed with 5 ml of deionized water and the eluate is discarded. The columns are then eluted with 6.0 ml of a solvent mixture (acetonitrite:$H_2O$:acetic acid in the proportion 50:50:0.1) which recovers all the arachidonic acid metabolites including 5-HETE and $LTB_4$ with very little of arachidonic acid (AA) being eluted (less than 2–3% of incubated counts). The columns are then eluted with 2.0 ml of methanol (forced through by $N_2$) which elutes all of the unreacted substrate AA. The eluates are collected in scintillation vials and 1.0 ml aliquot from each of the two fractions are counted for radioactivity in a Packard liquid scintillation counter. From the radioactivity data thus obtained percent yields of total lipoxygenase products in blanks, controls and drug containing tubes are calculated as well as percent inhibition by the test compounds.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings.

What is claimed is:

1. A composition of matter comprising:
   a compound having a formula represented by:

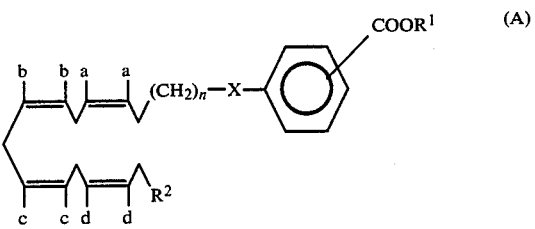

wherein:
n is an integer equal to zero, 1, 2 or 3;
X is S, O, or $CH_2$;
$R^1$ is hydrogen, lower alkyl or a pharmaceutically acceptable cation;
$R^2$ is lower alkyl, or

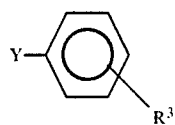

wherein Y is —O— or —S—; and $R^3$ is hydrogen, lower alkyl, lower alkoxy, lower alkylthio, halo, cyano or trifluoromethyl; and each pair of a—a, b—b, c—c, and d—d is independently hydrogens or a covalent bond.

2. The compound of claim 1 wherein n is zero.

3. The compound of claim 2 wherein a—a, b—b, c—c, and d—d are all hydrogen.

4. The compound of claim 3 wherein X is S.

5. The compound of claim 4 wherein $R^1$ is hydrogen and $R^2$ is n-butyl namely 2-heptadeca-2'(Z),5'(Z),8'(Z),11'(Z)-tetraenylthio)benzoic acid.

6. The compound of claim 4 wherein $R^1$ is hydrogen and $R^2$ is n-butyl namely, 3-(heptadeca-2'(Z),5'(Z),8'(Z),11'(Z)-tetraenylthio)benzoic acid.

7. The compound of claim 3 wherein X is O.

8. The compound of claim 7 wherein $R^1$ is hydrogen and $R^2$ is n-butyl namely 2-heptadeca-2'(Z),5'(Z),8'(Z),11'(Z)tetraenyloxy) benzoic acid.

9. The compound of claim 8 wherein $R^1$ is hydrogen and $R^2$ is phenoxy, namely 2-(13'-phenoxytrideca-2'(Z),5'(Z),8'(Z),11'(Z)-tetraenyloxy)benzoic acid.

10. The compound of claim 8 wherein $R^1$ is hydrogen and $R^2$ is phenoxy, namely, 3-(13'-phenoxytrideca-2'(Z),5'(Z),8'(Z),11'(Z)-tetraenyloxy)benzoic acid.

11. The compound of claim 1 wherein n is 3, X is S, $R^1$ is hydrogen and $R^2$ is n-butyl, namely 2-(eicosa-5'(Z),8'(Z),11'(Z),14'(Z)-tetraenylthio)benzoic acid.

12. The compound of claim 3 wherein X is $CH_2$.

13. The compound of claim 12 wherein $R^1$ is hydrogen and $R^2$ is n-butyl namely, 2-(octadeca-3'(Z),6'(Z),9'(Z),12'(Z)-tetraenyl)benzoic acid.

14. The compound of claim 1 wherein at least one of the pairs of a—a, b—b, and c—c is a covalent bond and each d—d is hydrogen.

15. The compound of claim 14 wherein a—a is a covalent bond and n is 0.

16. The compound of claim 15 wherein X is O, $R^1$ is hydrogen and $R^2$ is n-butyl, namely 2-(heptadeca-5'(Z),8'(Z),11'(Z)-triene-2'-ynyloxy)benzoic acid.

17. The compound of claim 15 wherein X is $CH_2$, $R^1$ is hydrogen, and $R^2$ is n-butyl, namely 2-(octadeca 6'(Z),9'(Z),12'(Z)-triene-3'-ynyl)benzoic acid.

18. The compound of claim 15 wherein X is S.

19. The compound of claim 18 wherein $R^1$ is hydrogen and $R^2$ is phenoxy, namely 2-(13'-phenoxytrideca-5'(Z),8'(Z),11'(Z)-triene-2-ynylthio)benzoic acid.

20. The compound of claim 18 wherein $R^1$ is hydrogen and $R^2$ is n-butyl namely 2-(heptadeca-5'(Z),8'(Z),11'(Z)-triene-2'-ynylthio)benzoic acid.

21. The compound of claim 18 wherein $R^1$ is hydrogen and $R^2$ is n-butyl, namely, 3-(heptadeca-5'(Z),8'(Z),11'(Z)-triene-2'-ynylthio)benzoic acid.

22. The compound of claim 18 wherein $R^1$ is hydrogen and $R^2$ is n-pentyl, namely, 2-(octadeca-5'(Z),8'(Z),11'(Z)triene-2'-ynylthio)benzoic acid.

23. The compound of claim 14 wherein b—b is a covalent bond and X is S and n is 0.

24. The compound of claim 23 wherein $R^1$ is hydrogen and $R^2$ is n-butyl, namely, 2-(heptadeca-2'(Z),8'(Z),11'(Z)-triene-5'-ynylthio)benzoic acid.

25. The compound of claim 23 wherein $R^1$ is hydrogen and $R^2$ is n-butyl, namely, 3-(heptadeca-2'(Z),8;(Z),11'(Z)-triene-5-ynylthio)benzoic acid.

26. The compound of claim 14 wherein each of the pairs a—a and c—c is a covalent bond and b—b is hydrogen.

27. The compound of claim 26 wherein n is zero, X is S, R is H and $R^2$ is n-butyl namely, 2-(Heptadeca-5'(Z),11'(Z)-dien-2',8'-diynylthio)benzoic acid.

28. A method of treating a mammal having a disease state characterized by overproduction of the products of lipoxygenase metabolism of arachidonic acid, which method comprises administering a compound of claim 1 to the animal.

29. The method of claim 28 wherein said disease state is an inflammatory disease.

30. The method of claim 28 wherein said disease state is rheumatoid arthritis.

31. The method of claim 28 wherein said disease state is asthma.

32. The method of claim 28 wherein said disease state is thrombosis.

33. A pharmaceutical formulation comprising a compound of claim 1 and a pharmaceutically acceptable excipient.

* * * * *